US012605114B2

(12) United States Patent
Qin

(10) Patent No.: US 12,605,114 B2
(45) Date of Patent: Apr. 21, 2026

(54) COMPLETE ECG CONTACT IMPEDANCE DETERMINATION

(71) Applicant: Drägerwerk AG & Co. KGaA, Lübeck (DE)

(72) Inventor: Derek Y. Qin, Andover, MA (US)

(73) Assignee: Dragerwerk AG & Co. KGaA, Lübeck (DE)

( * ) Notice: Subject to any disclaimer, the term of this patent is extended or adjusted under 35 U.S.C. 154(b) by 533 days.

(21) Appl. No.: 18/073,173

(22) Filed: Dec. 1, 2022

(65) Prior Publication Data

US 2023/0172548 A1 Jun. 8, 2023

Related U.S. Application Data

(60) Provisional application No. 63/286,471, filed on Dec. 6, 2021.

(51) Int. Cl.
| | |
|---|---|
| *A61B 5/0531* | (2021.01) |
| *A61B 5/00* | (2006.01) |
| *A61B 5/28* | (2021.01) |
| *A61B 5/339* | (2021.01) |

(52) U.S. Cl.
CPC .......... *A61B 5/6843* (2013.01); *A61B 5/0531* (2013.01); *A61B 5/28* (2021.01); *A61B 5/339* (2021.01); *A61B 2562/04* (2013.01); *A61B 2562/222* (2013.01)

(58) Field of Classification Search
CPC ............................. A61B 5/0531; A61B 5/318
See application file for complete search history.

(56) References Cited

U.S. PATENT DOCUMENTS

2016/0128635 A1* 5/2016 Sunderland ............ A61B 5/053
600/393

* cited by examiner

*Primary Examiner* — George R Evanisko
(74) *Attorney, Agent, or Firm* — Nolte Lackenbach Siegel

(57) ABSTRACT

An ECG monitoring method and apparatus are presented in which contact impedances including capacitive components are utilized to, for example, reduce false alarms for lead-off conditions. In one aspect of the disclosure a method includes monitoring a plurality of Electrocardiogram ("ECG") electrodes ostensibly electrically connected to a human body; determining the respective contact impedance for each of the ECG electrodes as a plurality of electrical currents is driven through the ECG electrodes in a predetermined pattern, each respective contact impedance including a resistive component and a capacitive component; ascertaining whether any of the determined respective contact impedances exceeds a predetermined threshold; if any of the determined respective contact impedances exceeds the predetermined threshold, issuing an alarm.

14 Claims, 4 Drawing Sheets

100

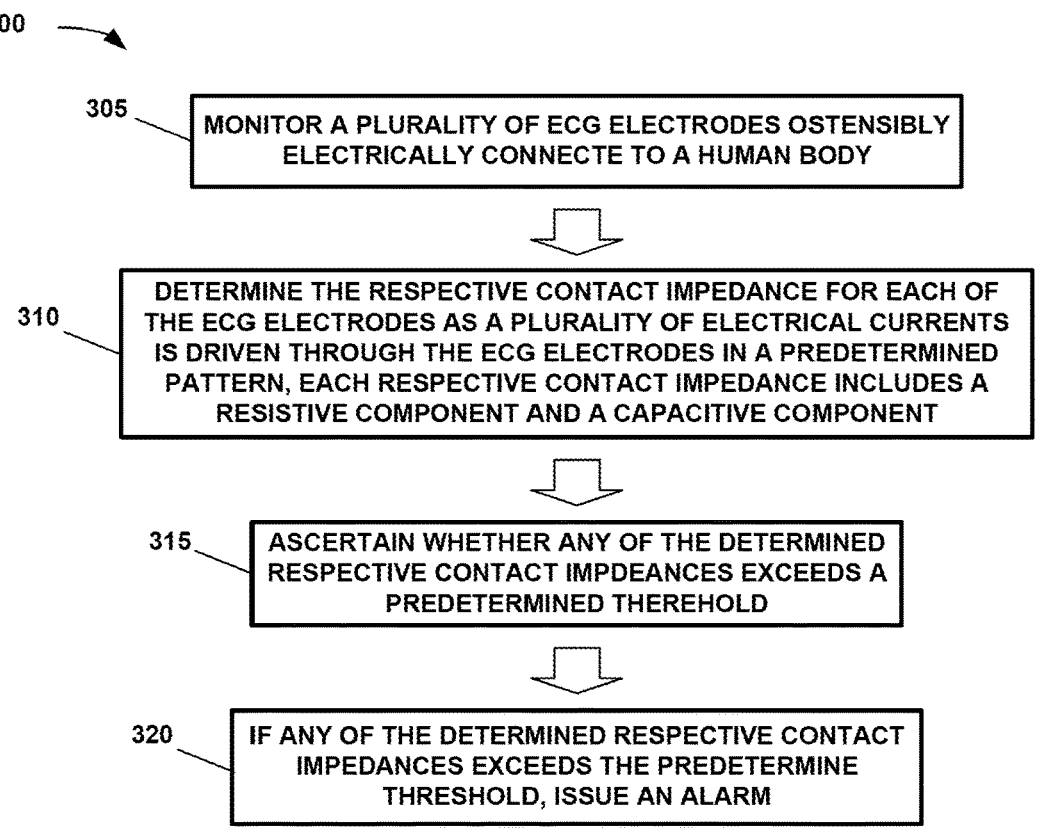

300

305 — MONITOR A PLURALITY OF ECG ELECTRODES OSTENSIBLY ELECTRICALLY CONNECTE TO A HUMAN BODY

310 — DETERMINE THE RESPECTIVE CONTACT IMPEDANCE FOR EACH OF THE ECG ELECTRODES AS A PLURALITY OF ELECTRICAL CURRENTS IS DRIVEN THROUGH THE ECG ELECTRODES IN A PREDETERMINED PATTERN, EACH RESPECTIVE CONTACT IMPEDANCE INCLUDES A RESISTIVE COMPONENT AND A CAPACITIVE COMPONENT

315 — ASCERTAIN WHETHER ANY OF THE DETERMINED RESPECTIVE CONTACT IMPDEANCES EXCEEDS A PREDETERMINED THEREHOLD

320 — IF ANY OF THE DETERMINED RESPECTIVE CONTACT IMPEDANCES EXCEEDS THE PREDETERMINE THRESHOLD, ISSUE AN ALARM

FIGURE 3

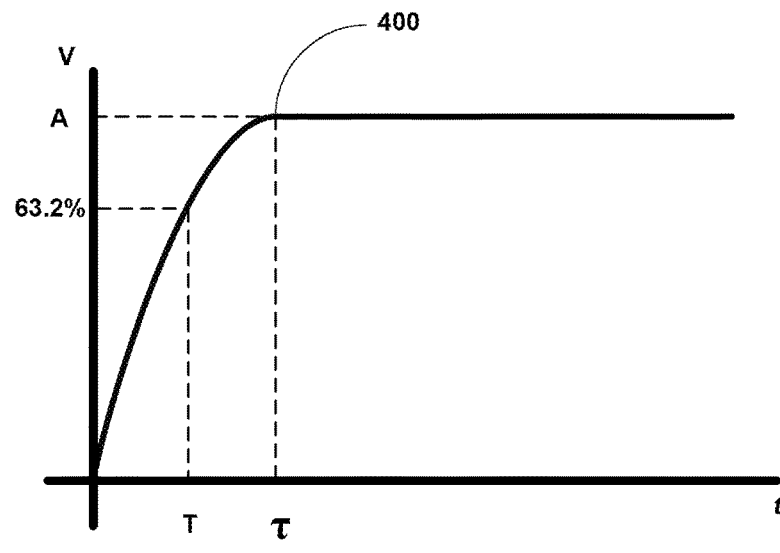

FIGURE 4

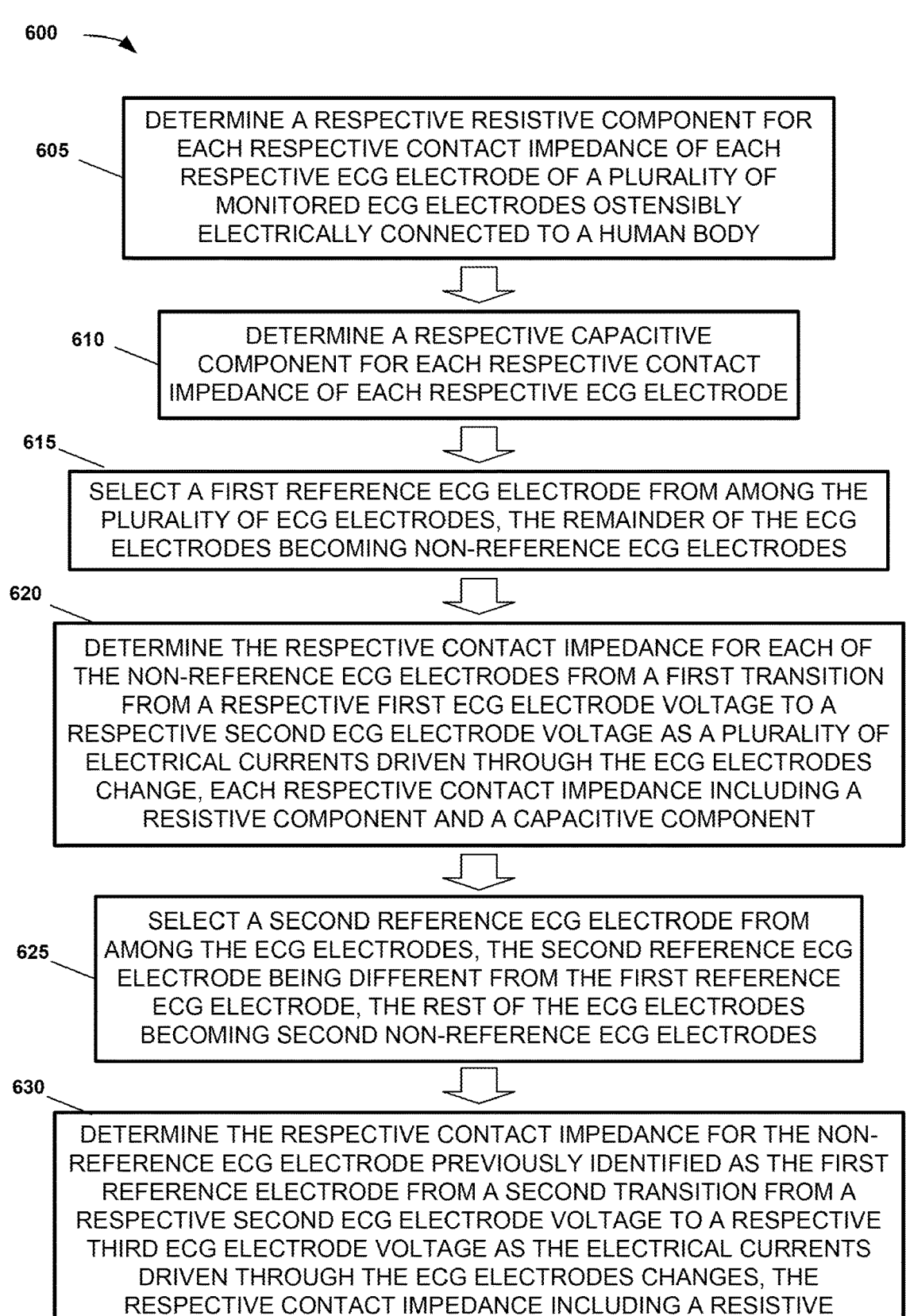

600

605 — DETERMINE A RESPECTIVE RESISTIVE COMPONENT FOR EACH RESPECTIVE CONTACT IMPEDANCE OF EACH RESPECTIVE ECG ELECTRODE OF A PLURALITY OF MONITORED ECG ELECTRODES OSTENSIBLY ELECTRICALLY CONNECTED TO A HUMAN BODY

610 — DETERMINE A RESPECTIVE CAPACITIVE COMPONENT FOR EACH RESPECTIVE CONTACT IMPEDANCE OF EACH RESPECTIVE ECG ELECTRODE

615 — SELECT A FIRST REFERENCE ECG ELECTRODE FROM AMONG THE PLURALITY OF ECG ELECTRODES, THE REMAINDER OF THE ECG ELECTRODES BECOMING NON-REFERENCE ECG ELECTRODES

620 — DETERMINE THE RESPECTIVE CONTACT IMPEDANCE FOR EACH OF THE NON-REFERENCE ECG ELECTRODES FROM A FIRST TRANSITION FROM A RESPECTIVE FIRST ECG ELECTRODE VOLTAGE TO A RESPECTIVE SECOND ECG ELECTRODE VOLTAGE AS A PLURALITY OF ELECTRICAL CURRENTS DRIVEN THROUGH THE ECG ELECTRODES CHANGE, EACH RESPECTIVE CONTACT IMPEDANCE INCLUDING A RESISTIVE COMPONENT AND A CAPACITIVE COMPONENT

625 — SELECT A SECOND REFERENCE ECG ELECTRODE FROM AMONG THE ECG ELECTRODES, THE SECOND REFERENCE ECG ELECTRODE BEING DIFFERENT FROM THE FIRST REFERENCE ECG ELECTRODE, THE REST OF THE ECG ELECTRODES BECOMING SECOND NON-REFERENCE ECG ELECTRODES

630 — DETERMINE THE RESPECTIVE CONTACT IMPEDANCE FOR THE NON-REFERENCE ECG ELECTRODE PREVIOUSLY IDENTIFIED AS THE FIRST REFERENCE ELECTRODE FROM A SECOND TRANSITION FROM A RESPECTIVE SECOND ECG ELECTRODE VOLTAGE TO A RESPECTIVE THIRD ECG ELECTRODE VOLTAGE AS THE ELECTRICAL CURRENTS DRIVEN THROUGH THE ECG ELECTRODES CHANGES, THE RESPECTIVE CONTACT IMPEDANCE INCLUDING A RESISTIVE COMPONENT AND A CAPACITIVE COMPONENT

FIGURE 6

COMPLETE ECG CONTACT IMPEDANCE DETERMINATION

CROSS-REFERENCE TO RELATED APPLICATIONS

The priority of U.S. Application Ser. No. 63/286,471, filed Dec. 6, 2021, is hereby claimed under 35 U.S.C. 119 (e) and is incorporated by reference for all purposes.

TECHNICAL FIELD

The present disclosure pertains to electrocardiogram monitoring and, more specifically, to contact impedance measurement during an electrocardiogram procedure.

DESCRIPTION OF THE RELATED ART

This section of this document introduces information about and/or from the art that may provide context for or be related to the subject matter described herein and/or claimed below. It provides background information to facilitate a better understanding of the various aspects of the that which is claimed below. This is a discussion of "related" art. That such art is related in no way implies that it is also "prior" art. The related art may or may not be prior art. The discussion in this section of this document is to be read in this light, and not as admissions of prior art.

An electrocardiogram ("ECG") graphs voltage acquired from a person's body over time. The voltages represent electrical activity of the heart. To acquire the voltages, electrodes are placed at selected points on the person's body. It is desirable to establish a strong physical contact and electromagnetic coupling between each of the electrodes and the person's body. The strong physical contact and electromagnetic coupling are desirable because they promote good data acquisition that improves the accuracy of the ECG.

One measure of the strength of the contact and the coupling is "contact impedance", There inherently exists an impedance at the interface between the electrode and the skin and this impedance is called the contact impedance. A low contact impedance is desirable because it indicates a strong physical contact and electromagnetic coupling. Conversely, a high impedance is undesirable and may even indicate a "lead-off" condition. A lead-off condition is a condition in which the electrode has become detached from the person's body to the point it no longer adequately acquires the voltages.

Many ECG monitors therefore monitor the contact impedance of the various electrodes during the ECG procedure. If a contact impedance exceeds some predetermined threshold, the ECG monitor may presume it indicates that a lead is off and issue an alarm. An attendant or technician, upon detecting the alarm, may then check to make sure there are no detached electrodes and, if there are, then reattach them.

BRIEF DESCRIPTION OF THE DRAWINGS

Illustrative embodiments of the subject matter claimed below will now be disclosed. In the interest of clarity, not all features of an actual implementation are described in this specification. It will be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure, FIG. 1 conceptually depicts an ECG procedure in accordance with the present disclosure.

FIG. 3 illustrates a method for performing an ECG procedure according to one embodiment of the present disclosure.

FIG. 4 depicts the change over time in a voltage measure by an ECG electrode as a driving current changes.

FIG. 6 illustrates a method for determining the capacitive element of an ECG contact impedance according to one embodiment of the present disclosure.

While the invention is susceptible to various modifications and alternative forms, the drawings illustrate specific examples herein described in detail by way of example. It should be understood, however, that the description herein of specific examples is not intended to limit the invention to the particular forms disclosed, but on the contrary, the intention is to cover all modifications, equivalents, and alternatives falling within the spirit and scope of the invention as defined by the appended claims.

DETAILED DESCRIPTION

As alluded to above, ECG monitors may monitor contact impedance to determine whether a lead-off condition has occurred. The contact impedance has both a resistive component and a capacitive component. However, known monitoring techniques only use the resistive component of the contact impedance. There is an underlying assumption that when the resistive component is high the capacitive component is low and vice versa. Under this assumption, the case in which both the resistive component and the capacitive component are high then overall contact impedance is also high. This is not always correct.

If the resistive component is low and the capacitive component is low, the overall contact impedance is low and performance is high. When the resistive component is low and the capacitive component is low, or when the resistive component is high and the capacitive component is high, the overall contact impedance can be low and therefore good for performance. In some cases, when the resistive component is high and the capacitive component is low it is possible that the contact impedance may get high enough to degrade performance. Thus, the underlying assumption mentioned above can lead to undesirable false alarms for the presence of a lead-off condition.

The presently disclosed technique includes a determination of the capacitive component of the contact impedance that can be combined with the resistive component to obtain a more accurate measure of a contact impedance. Although the presently disclosed technique determines the resistive component in the course of determining the capacitive component, this is not always necessary. The resistive component may be determined in any manner known to the art. One suitable technique is disclosed in U.S. Letters Patent 10,368,805 issued Aug. 6, 2019, to Draegerwerk AG & Co. KGAA as assignee of the inventor Derek Y. Qin ("the '805 patent"). This patent is hereby incorporated by reference for all purposes as if set forth verbatim herein. By operating on a contact impedance including both the resistive and capacitive elements, a more accurate determination of whether a lead-off condition is present can be made. This, in turn, may reduce the occurrence of false alarms.

Figure 1:
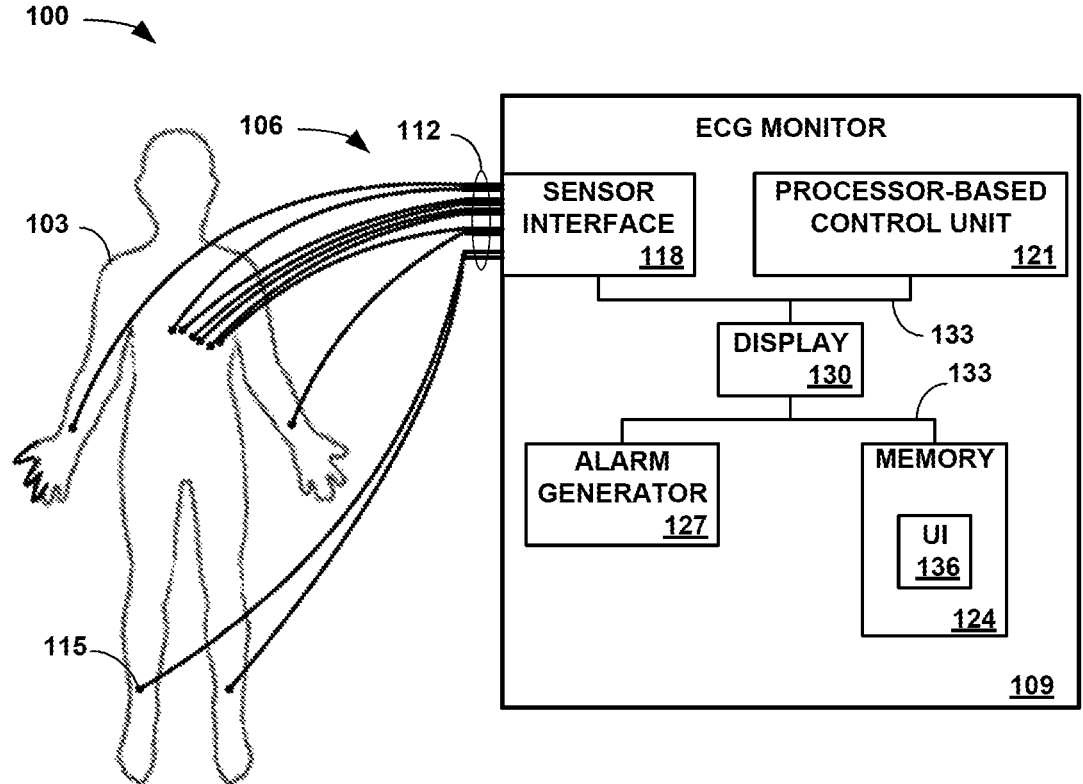

Turning now to the drawings, FIG. 1 illustrates an ECG procedure 100 in accordance with the present disclosure. In FIG. 1, a patient 103 is undergoing the ECG procedure 100 being administered using the ECG system 106. The ECG system 106 comprises an ECG monitor 109, a plurality of electrical leads 112, and a plurality of ECG electrodes 115 (only one indicated). There need not be a 1:1 correspondence between the ECG electrodes 115 and the electrical leads 112 as is shown in FIG. 1. The ECG electrodes 115 are ostensibly attached to the patient 103 and connected to the EGG monitor 109 via the electrical leads 112.

As used herein, the term "ostensibly attached" means that the ECG electrodes 115 are intended to physically contact and electromagnetically couple to the body of the patient 103 sufficiently to acquire suitable EGG data during the ECG procedure 100. However, as described above, it is possible that one or more of the ECG electrodes 115 may become detached from the body of the patient 103 to a problematical degree. The present disclosure is directed to a technique by which the ECG monitor 109 may determine whether a high-impedance or even lead-off condition is present. In such a situation, while it is intended that the ECG electrodes 115 are to be attached, one or more may be detached. The term "ostensibly attached" describes this situation.

The implementation of the ECG electrodes 115 and the electrical leads 112 will depend on the configuration of the ECG system 106 in a manner that will become apparent to those skilled in the art having the benefit of this disclosure. For example, the ECG electrodes 112 may be, without limitation, a flat, paper-thin sticker or a self-adhesive circular pad. The electrical leads 112 may be, again without limitation, limb leads, augmented limb leads, precordial (or chest) leads, or some combination of these. One common configuration, and one with which the currently disclosed technique may be practiced, is a 10 electrode, 12 lead configuration to measure 10 voltages across a person's body. One example of what the 10 electrodes may measure is set forth in Table 1 below. Note that the nomenclature used in Table 1 may differ from that used conventionally to prevent confusion and make consistent with other nomenclature used below.

TABLE 1

Example ECG Electrode Placements

| Electrode Name | Placement |
| --- | --- |
| RA | Right arm. |
| LA | Left arm, corresponding location as the right arm. |
| RL | Right leg, lower end of the calf muscle on the inside of the leg. |
| LL | Left leg, corresponding location to the right leg. |
| $E_1$ | Fourth intercoastal space between the fourth and fifth ribs, to the right of the sternum. |
| $E_2$ | Fourth intercoastal space between the fourth and fifth ribs, to the left of the sternum. |
| $E_3$ | Between $E_1$ and $E_4$. |
| $E_4$ | Fifth intercoastal space between the fifth and sixth ribs in the mid-clavicular line. |
| $E_5$ | Horizontally even with $E_4$ in the left anterior axillary line. |
| $E_6$ | Horizontally even with $E_4$ and $E_5$ in the mid-axillary line. |

The ECG monitor 109 includes, in this particular example, at least a sensor interface 118, a processor-based control unit 121, a memory 124, and an alarm generator 127. In some embodiments, the memory 124 and alarm generator 127 may be incorporated into the processor-based control unit 121. Although not necessary to practice the technique disclosed herein, the ECG monitor 109 also includes a display 130. The display 130 may be used to present a user interface ("UI", not separately shown) through which a user may interact with the ECG monitor 109. The various components of the ECG monitor 109 may communicate with one another over a bus system 133.

The display 130 may be any suitable type of display known to the art. The display may be, for example and without limitation, a Light Emitting Diode ("LED") display, a Liquid Crystal Display ("LCD"), an electroluminescent display, or even a cathode-ray tube display. The display 130 may be a touch screen in some embodiments and may not be in other embodiments. Embodiments in which the display 130 is a touch screen may be used to present a Graphical User Interface ("GUI"). In embodiments in which the display 130 is not a touch screen, the UI may include mechanical means, such as buttons and/or switches, to interface with a user. Regardless of whether the display 130 includes a touch screen, various embodiments may also employ a variety of peripheral input devices (not shown) as a part of the UI. Examples of such peripheral input devices include, without limitation, pointing devices such a mouse, trackpad, or track ball and keyboards.

As with the display 130 and the UI, the technique disclosed herein also admits wide variation in the implementation of the alarm generator 127. The alarm generator 127 may be, for example, an audio speaker to broadcast an audio alarm. In other examples, the alarm generator 127 may include a light, such as an LED, to provide a visual alarm. Note that, in some embodiments, a visual alarm may be presented on the display 130 through the UI such that the alarm generator 127 may be omitted. Furthermore, such a visual alarm may include a display of the contact impedance demonstrating that it exceeds a threshold as is discussed below.

The sensor interface 118 receives data from the ECG electrodes 115 over the leads 112 and then conditions that data for use and handling by the rest of the ECG monitor 109. The sensor interface 118 may include, for example, one or more electrical connectors (not separately shown) the receive(s) and/or mates with one or more electrical connectors (also not separately shown) that may comprise a part of the electrical leads 112. The sensor interface 118 may also include electrical circuitry and electronic components for conditioning the received data. As those in the art having the benefit of this disclosure will appreciate, the precise makeup of the sensor interface 118 in any given embodiment will be implementation specific. Factors for consideration may include, without limitation, the quantity, quality, form, and format of the received data.

Those in the art having the benefit of this disclosure will also appreciate that the ECG monitor 109 will typically include other components not separately shown. For example, the ECG monitor 109 may include a battery, a connection to a power supply such as an electrical grid, or both. Similarly, the ECG monitor 109 may also include mechanical buttons or switches for a user to interact with the ECG monitor 109 during use as mentioned above. However, these and other features of the ECG monitor 109 not germane to the practice of the technique disclosed herein have been omitted for the sake of clarity and to promote an understanding of that which is claimed below.

Figure 2:
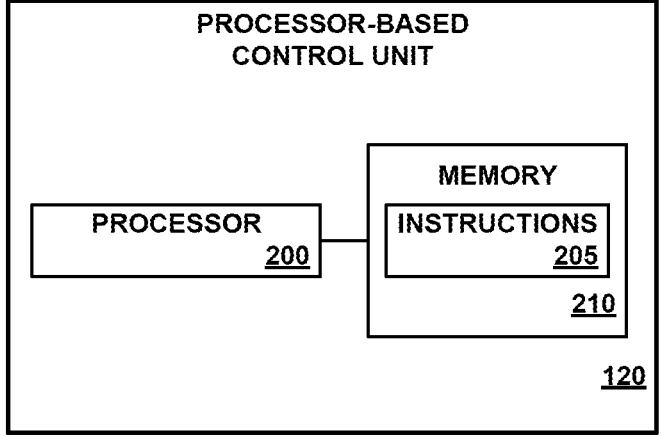
FIG. 2 conceptually illustrates one particular implementation of the processor-based control unit of FIG. 1.

FIG. 2 conceptually illustrates one particular implementation of the processor-based control unit 121. In the illustrated embodiment, the processor-based controller 121 is dedicated to performing the functional aspects of the technique disclosed herein. However, in alternative embodiments, the processor-based control unit 121 may also more generally perform all control functions for the ECG monitor 109 in addition to the technique disclosed herein. For example, in some embodiments, the processor-based control unit 121 may present a user interface (not separately shown) to a user on the display 130 by executing a set of user interface ("UI") instructions 136 residing in memory 124 as shown in FIG. 1.

As those in the art having the benefit of this disclosure will appreciate, the term "processor" is understood in the art to have a definite connotation of structure. A processor may be hardware, software, or some combination of the two. In the illustrated embodiment of FIG. 2, the processor 200 is a programmed hardware processor, such as a controller, a microcontroller or a Central Processing Unit ("CPU"). However, in alternative embodiments, the processor 200 may be a Digital Signal Processor ("DSP"), a processor chip set, an Application Specific Integrated Circuit ("ASIC"), an appropriately programmed Electrically Programmable Read-Only Memory ("EPROM"), an appropriately programmed Electrically Erasable, Programmable Read-Only Memory ("EE-PROM"), a logic circuit, etc.

The processor 200 executes machine executable instructions 205 residing in the memory 210 to perform the functionality of the technique described herein. The instructions 205 may be embedded as firmware in the memory 210 or encoded as routines, subroutines, applications, etc. The memory 210, as well as the memory 124 in embodiments where they differ, may include Read-Only Memory ("ROM"), Random Access Memory ("RAM"), or a combination of the two. They will typically be installed memory but may be removable. They may be primary storage, secondary, tertiary storage, or some combination thereof implemented using electromagnetic, optical, or solid-state technologies.

Accordingly, in the illustrated embodiment, the processor-based control unit 121 performs the software-implemented functionality of the presently disclosed technique. More particularly, the processor 200 executes the instructions 205, both shown in FIG. 2, to perform the programmed functionality in which the ECG monitoring process includes a determination of the capacitive component of the contact impedance. The capacitive component can then be combined with the resistive component to get a more accurate measure of a contact impedance.

Referring now to FIG. 1 and FIG. 3 collectively, in some embodiments, the processor-based control unit 121 performs the method 300 during the ECG procedure 100. The method 300 begins by monitoring (at 305) the ECG electrodes 115 ostensibly electrically connected to the body of the patient 103. As described above, during the ECG procedure 100, the ECG electrodes 115 are presumed to be attached but it is possible that one or more of the ECG electrodes 115 may have become detached. Thus, the ECG electrodes 115 are, for purposes of the presently disclosed technique, considered to be "ostensibly connected".

The method 300 continues by determining (at 310) the respective contact impedance for each of the ECG electrodes 115 as electrical currents are driven through them in a predetermined pattern. As discussed above, the predestined pattern includes both values and sequencing. Each respective contact impedance includes a resistive component and a capacitive component. One method for determining the capacitive component will be discussed further below. As mentioned above, the resistive component may be determined in any manner known to the art, such as is disclosed in the '805 patent.

The method 300 also ascertains (at 315) whether any of the determined respective contact impedances for the ECG electrodes 115 exceeds a predetermined threshold. The measure of the predetermined threshold may vary depending how closely any given implementation wishes to monitor the ECG procedure 100 for lead-off conditions. In particular, an alarm is issued when the resistive component of the contact impedance is high and the capacitive component is low. Thus, some embodiments may set the predetermined threshold at greater than 4M0 and less than 5 nF, for example.

If (at 320) any of the determined respective contact impedances exceeds the predetermined threshold, an alarm is issued. The alarm may be, for example, an audio alarm, a visual alarm, or a combination of the two. The alarm may be issued by the alarm generator 127 at the direction of the processor-based control unit 121 or, in some embodiments, the processor-based control unit 121 itself.

Thus, the presently disclosed technique provides a method for a determining the capacitive component of a contact impedance for each of a plurality of ECG electrodes during an ECG procedure. The capacitive component can then be combined with the resistive component to get a more accurate measure of a contact impedance. The technique also provides an ECG system for performing such a method during an ECG procedure. In some aspects, the presently disclosed technique also provides a computer-readable medium (e.g., the memory 124 or the memory 210) encoded with instructions perform such a method.

One particular way in which the capacitive component of a contact impedance can be determined will now be disclosed. The capacitive component is non-linear and behaves non-linearly in the face of changes in voltage. FIG. 4 illustrates the change in a voltage over time t as it reaches a steady state, direct current ("DC") value A at point 400. The quantity r represents the time at which the curve has settled enough that the contact impedance may be determined for purposes of determining a lead-off condition.

The voltage is an exponential function $f(t)$ that can be represented as:

$$f(t) = A\left(1 - e^{-\frac{t}{\tau}}\right) \tag{1}$$

Since the curve in FIG. 4 is exponential, the quantity T can be calculated from three samples of the curve shown in FIG. 4. For a sample period:

$$T_s = \frac{1}{f_s} \tag{2}$$

The contact impedance Z(x) for the three samples n to n+2 may be represented by Equations (3)-(5):

$$Z(n) = A\left(1 - e^{-\frac{nT_s}{\tau}}\right) \tag{3}$$

-continued $$Z(n+1) = A\left(1 - e^{-\frac{(n+1)T_s}{\tau}}\right) \tag{4}$$

$$Z(n+2) = A\left(1 - e^{-\frac{(n+2)T_s}{\tau}}\right) \tag{5}$$

The quantity $\tau$ can then be calculated as follows. First, the difference between $Z(n+1)$ and $Z(n)$ and between $Z(n+2)$ and $Z(n+1)$ are taken:

$$Z_{n+1} - Z_n = A\left[e^{-\frac{nT_s}{\tau}} - e^{-\frac{(n+1)T_s}{\tau}}\right] \tag{6}$$

$$= Ae^{-\frac{(n+1)T_s}{\tau}}\left[e^{\frac{T_s}{\tau}} - 1\right] \tag{7}$$

$$Z_{n+2} - Z_{n+1} = A\left[e^{-\frac{(n+1)T_s}{\tau}} - e^{-\frac{(n+2)T_s}{\tau}}\right] \tag{8}$$

$$= Ae^{-\frac{(n+1)T_s}{\tau}}\left[1 - e^{-\frac{T_s}{\tau}}\right] \tag{9}$$

A quantity q is then represented as:

$$q = \frac{Z_{n+2} - Z_{n+1}}{Z_{n+1} - Z_n} \tag{10}$$

Substituting Equations (7) and (9) and reducing yields:

$$q = \frac{Ae^{-\frac{(n+1)T_s}{\tau}}\left[1 - e^{-\frac{T_s}{\tau}}\right]}{Ae^{-\frac{(n+1)T_s}{\tau}}\left[e^{\frac{T_s}{\tau}} - 1\right]} \tag{11}$$

$$= \frac{1 - e^{-\frac{T_s}{\tau}}}{e^{\frac{T_s}{\tau}} - 1} \tag{12}$$

Note that Equation (12) is independent of n. Next, define x as follows:

$$x = e^{-\frac{T_s}{\tau}} \tag{13}$$

Substituting Equation (13) into Equation (12) using x and reducing yields:

$$q = \frac{1 - x}{\frac{1}{x} - 1} \tag{14}$$

$$= \frac{x - x^2}{x} \tag{15}$$

$$= x \tag{16}$$

Substituting for x yields:

$$q = e^{-\frac{T_s}{\tau}} \tag{17}$$

Now:

$$\ln q = -\frac{T_s}{\tau} \tag{18}$$

And solving Equation (18) for $\tau$ yields:

$$\tau = -\frac{T_s}{\ln q} \tag{19}$$

Substituting Equation (10) for q:

$$\tau = -\frac{T_s}{\ln\frac{Z_{n+2} - Z_{n+1}}{Z_{n+1} - Z_n}} \tag{20}$$

From the determined value for $\tau$, the value for the DC voltage A can also then be determined. Using the equations above:

$$Z_n - A = -Ae^{-\frac{nT_s}{\tau}} \tag{21}$$

$$Z_{n+1} - A = -Ae^{-\frac{(n+1)T_s}{\tau}} \tag{22}$$

Then:

$$\frac{Z_n - A}{Z_{n+1} - A} = e^{\frac{T_s}{\tau}} \tag{23}$$

$$= \frac{1}{q} \tag{24}$$

It then follows that:

$$qZ_n - qA = Z_{n+1} - A \tag{25}$$

Solving for A:

$$A = \frac{Z_{n+1} - qZ_n}{1 - q} \tag{26}$$

Thus, instead of waiting for the voltage to reach a steady state DC voltage A, three samples of the voltage may be taken during the transition caused by changing a driving current as discussed below. From these three samples of the voltage in transition, both and A can be determined.

Figure 5:
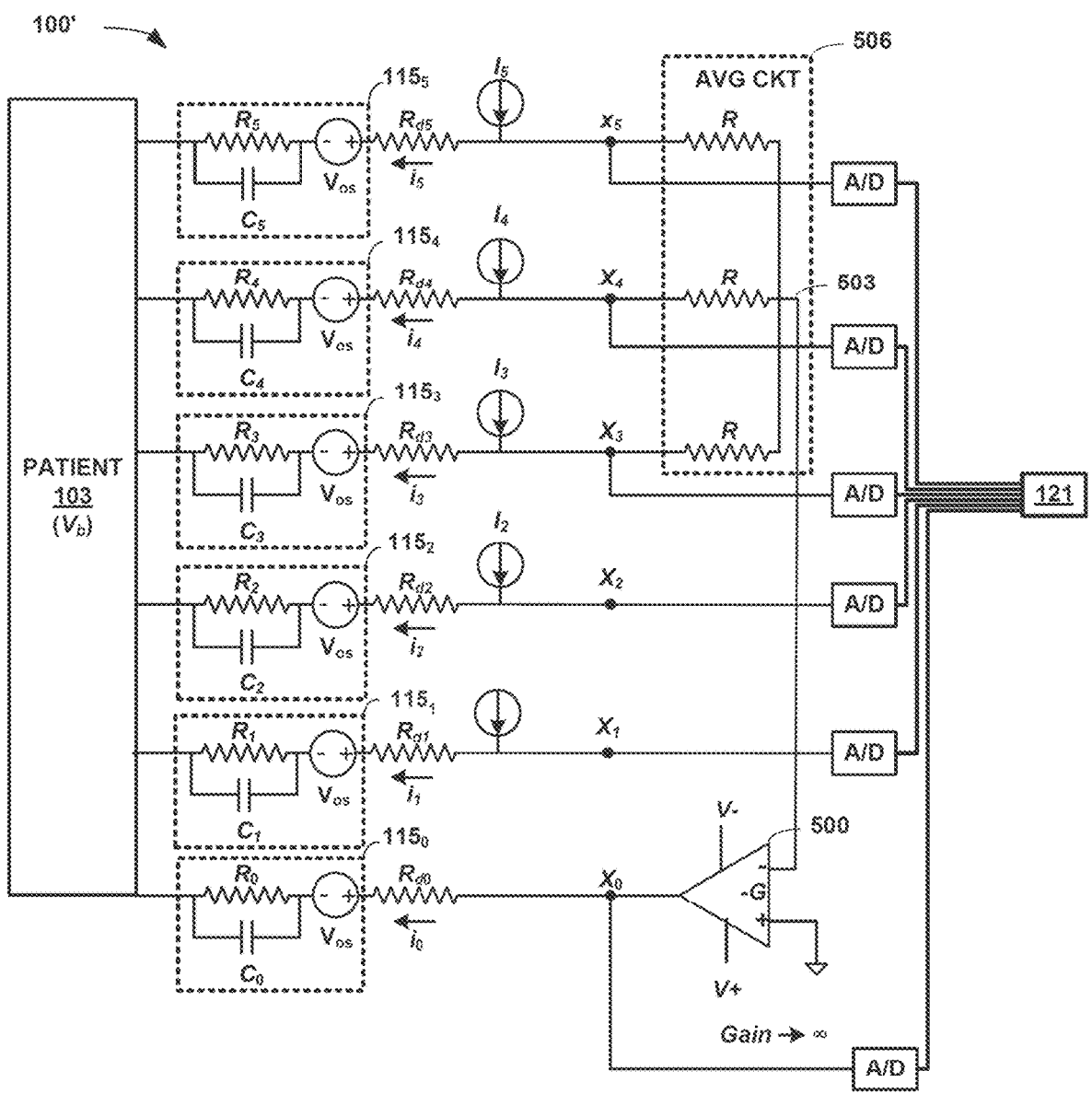
FIG. 5 is a conceptual diagram of selected portions of the ECG system of FIG. 1 in accordance with the present disclosure.

FIG. 5 is a conceptual diagram of selected portions of the ECG system 100' in accordance with the present disclosure. The ECG system 100', as discussed above relative to ECG system 100, includes a plurality of ECG electrodes 115₀-115₅. There theoretically may be any number of electrodes greater than or equal to three. Those in the art having the benefit of this disclosure, however, will realize that there are practical limitations on the number of electrodes. Each of the ECG electrodes 115₀-115₅ is attached to the patient 103. In the embodiment of FIG. 5, in contrast, the ECG system 100' is configured with six electrodes in which ECG electrodes 115₀-115₃ may be the right leg, right arm, left arm, and left leg leads and ECG electrodes 115₄-115₅ may be any of the other voltage leads.

Although the number of electrodes in the embodiment of FIG. 5 is six, other embodiments may have other numbers of electrodes. Some embodiments may have as many as 10 electrodes, for example, as in the embodiment of FIG. 1 in which there are 10 ECG electrodes 115. The present disclosure may be readily extrapolated by those skilled in the art having the benefit of this disclosure to any other number of electrodes. In theory, the technique disclosed herein may be applied to any number of electrodes so long as that number exceeds or is equal to three.

Each ECG electrode $115_0$-$115_5$ may be represented by its resistive and capacitive components as well as an offset voltage. Thus, in FIG. 5, ECG electrode $115_5$ is represented by a resistance $R_5$ in parallel with a capacitance $C_5$, both in series with an offset voltage Vas; the ECG electrode $115_4$ is represented by a resistance $R_4$ in parallel with a capacitance $C_4$, both in series with an offset voltage Vos; and so forth down to ECG electrode $115_0$, which is represented by a resistance $R_0$ in parallel with a capacitance $C_0$, both in series with an offset voltage $V_{os}$. The resistances $R_{d5}$-$R_{d0}$ represent the line resistances of the individual leads to the ECG electrodes $115_0$-$115_5$.

Each ECG electrode $115_1$-$115_5$ is associated with and electrically coupled to a respective current source $I_1$-$I_5$ as shown, excepting only the ECG electrode $115_0$. The current sources $I_1$-$I_5$ may be direct current ("DC") sources. The current sources $I_1$-$I_5$ each drive or inject a respective current $I_1$-$I_5$ through each respective ECG electrode $115_1$-$115_5$ in a predetermined pattern as will be described below. The current sources $I_1$-$I_5$ driving the current $I_1$-$I_5$ through each respective ECG electrode $115_1$-$115_5$ generates a respective voltage $V_{x1}$-$V_{x5}$ that is sensed at the points $x_1$-$x_5$. Each of the sensed voltages $V_{x1}$-$V_{x5}$ is converted to digital by a respective analog-to-digital converter ("A/D") for input to the processor-based control unit 121 to implement the functionality described herein.

The ECG electrode $115_0$ receives a current $i_0$ from operational amplifier 500 driven by the voltage output 503 of averaging circuit ("AVG CKT") 506. The output 503 of the averaging circuit 506 is the average of the three voltages $V_{x3}$-$V_{x5}$ at points $x_3$-$x_5$ across the ECG electrodes $115_3$-$115_5$. The voltage output 503 may be a Wilson average voltage as described in WO 2015/153426, filed Mar. 30, 2015, entitled "Detecting Saturation in an Electrocardiogram Neutral Drive Amplifier," the entire contents of which are incorporated by reference herein. The resistance value of the resistors R in the averaging circuit 506 may be, for example, in the range of 10 kΩ to 100 kΩ.

For purposes of the following description of how the capacitive component $C_0$-$C_5$ of the contact impedance for each ECG electrode $115_0$-$115_5$ may be determined. The following description therefor assumes a configuration for the ECG system 100' in which there are six ECG electrodes. However, as discussed above, the value of ECG electrodes may vary depending upon the configuration of the ECG system 100'. Those in the art having the benefit of this disclosure will be able to readily adapt the following discussion for those configurations in which there are numbers of ECG electrodes other than six The technique assumes that the ECG system 100' is operating and has reached a steady state or that the steady state values have been determined using T is described above. This includes the current sources $I_1$-$I_5$ each driving a respective initial current $I_1$-$I_5$ through each respective ECG electrode $115_1$-$115_5$ and the operational amplifier 500 driving the initial current $I_0$ through ECG electrode $115_0$. The initial states of the voltages $V_{x0}$-$V_{x5}$ across the electrodes $115_0$-$115_5$ sensed at points $x_0$-$x_5$ in FIG. 5 may be represented by equations (27)-(32):

$$V_{x5}=V_b+V_{os5}+i_5R_{d5}+i_5Z_5 \tag{27}$$

$$V_{x4}=V_b+V_{os4}+i_4R_{d4}+i_4Z_4 \tag{28}$$

$$V_{x3}=V_b+V_{os3}+i_3R_{d3}+i_3Z_3 \tag{29}$$

$$V_{x2}=V_b+V_{os2}+i_2R_{d2}+i_2Z_2 \tag{30}$$

$$V_{x1}=V_b+V_{os1}+i_1R_{d1}+i_1Z_1 \tag{31}$$

$$V_{x0}=V_b+V_{os0}+i_0R_{d0}+i_0Z_0 \tag{32}$$

In equations (27)-(32), $V_b$ is the voltage across the body of the patient 103 and $V_{os}$ is the offset voltage of the respective ECG electrode 115. The contact impedances $Z_0$-$Z_5$ and the current $i_0$ is represented by equations (33)-(34), in which s=jω, the Laplace variable that represents frequency ω=2πf.

$$Z_i = \frac{R_i}{1 + sR_iC_i} \tag{33}$$

$$i_0 = -\sum_{j=1}^{5} i_j \tag{34}$$

After capturing the initial state of the ECG system 100', the technique makes a first pass in which certain, but not all, of the currents $i_0$-$i_5$ are changed. More particularly, one of the ECG electrodes $115_1$-$115_5$ is selected as a first reference ECG electrode for the first pass. Theoretically, the ECG electrode $115_0$ could be selected as the reference ECG electrode. However, because its driving current $i_0$ is dependent on the voltages $V_{x5}$-$V_{x3}$, the current $i_0$ is less easily controlled.

In the first phase, the injected current for the reference ECG electrode 115 is kept the same while the injected current for the remaining ECG electrodes 115 is changed. In this example, for illustrative purposes, the ECG Electrode $115_2$ is selected, and so the injected current $i_2$ remains unchanged. The injected currents $i_1$ and $i_3$-$i_5$ are then changed to $i_1'$ and $i_3'$-$i_5'$ which change $i_0$ to $i_0'$. For example, the injected currents might be "flipped". This causes the voltages $V_{x0}'$-$V_{x1}$ and $V_{x3}$-$V_{x5}$ to transition as shown in FIG. 4 and discussed above to $V_{x0}'$-$V_{x1}'$ and $V_{x3}'$-$V_{x5}'$. Note that $R_d$ and $V_{os}$ for each respective ECG electrode 115 will remain unchanged.

Accordingly, after the injected currents $i_1$ and $i_3$-$i_5$ are changed, the voltages $V_{x0}'$-$V_{x5}'$ may be represented as equations (35)-(40). Note that in equation (38), the injected current $i_2$ remains unchanged relative to equation (30) because the ECG electrode $115_2$ has been selected as the first reference ECG electrode.

$$V_{x5}'=V_b'+V_{os5}+i_5'R_{d5}+i_5'Z_5 \tag{35}$$

$$V_{x4}'=V_b'+V_{os4}+i_4'R_{d4}+i_4'Z_4 \tag{36}$$

$$V_{x3}'=V_b'+V_{os3}+i_3'R_{d3}+i_3'Z_3 \tag{37}$$

$$V_{x2}'=V_b'+V_{os2}+i_2'R_{d2}+i_2'Z_2 \tag{38}$$

$$V_{x1}'=V_b'+V_{os1}+i_1'R_{d1}+i_1'Z_1 \tag{39}$$

$$V_{x0}'=V_b'+V_{os0}+i_0'R_{d0}+i_0'Z_0 \tag{40}$$

The contact impedances $Z_0$-$Z_5$ in equations (35)-(40) are represented by equation (33) and the current $i_0'$ is represented by equation (41). Note, however, that, in application of equation (41), $i_2'=i_2$ as described above.

$$i_0' = -\sum_{j=1}^{5} i_j', \tag{41}$$

The initial voltage $V_{x2}$ across the first reference ECG electrode $115_2$ is subtracted from the initial voltages $V_{x0}$-$V_{x1}$ and $V_{x3}$-$V_{x5}$ across the ECG electrodes $115_0$-$115_1$ and $115_3$-$115_5$:

$$V_{x5}-V_{x2}=(V_{os5}-V_{os2})+(i_5R_{d5}-i_2R_{d2})+(i_5Z_5-i_2Z_2) \qquad (42)$$

$$V_{x4}-V_{x2}=(V_{os4}-V_{os2})+(i_4R_{d4}-i_2R_{d2})+(i_4Z_4-i_2Z_2) \qquad (43)$$

$$V_{x3}-V_{x2}=(V_{os3}-V_{os2})+(i_3R_{d3}-i_2R_{d2})+(i_3Z_3-i_2Z_2) \qquad (44)$$

$$V_{x1}-V_{x2}=(V_{os1}-V_{os2})+(i_1R_{d1}-i_2R_{d2})+(i_1Z_1-i_2Z_2) \qquad (45)$$

$$V_{x0}-V_{x2}=(V_{os0}-V_{os2})+(i_0R_{d0}-i_2R_{d2})+(i_0Z_0-i_2Z_2) \qquad (46)$$

Next, the voltage $V_{x2}'$ across the first reference ECG electrode $115_2$ from the first pass is subtracted from the initial voltages $V_{x0}$-$V_{x1}$ and $V_{x3}$-$V_{x5}'$ across the ECG electrodes $115_0$-$115_1$ and $115_3$-$115_5$ from the first pass.

$$V_{x5}'-V_{x2}'=(V_{os5}-V_{os2})+(i_5'R_{d5}-i_2R_{d2})+(i_5'Z_5-i_2Z_2) \qquad (47)$$

$$V_{x4}'-V_{x2}'=(V_{os4}-V_{os2})+(i_4'R_{d4}-i_2R_{d2})+(i_4'Z_4-i_2Z_2) \qquad (48)$$

$$V_{x3}'-V_{x2}'=(V_{os3}-V_{os2})+(i_3'R_{d3}-i_2R_{d2})+(i_3'Z_3-i_2Z_2) \qquad (49)$$

$$V_{x1}'-V_{x2}'=(V_{os1}-V_{os2})+(i_1'R_{d1}-i_2R_{d2})+(i_1'Z_1-i_2Z_2) \qquad (50)$$

$$V_{x0}'-V_{x2}'=(V_{os0}-V_{os2})+(i_0'R_{d0}-i_2R_{d2})+(i_0'Z_0-i_2Z_2) \qquad (51)$$

Equations (42)-(46) are then subtracted from equations (47)-(51), respectively.

$$(V_{x5}'-V_{x2}')-(V_{x5}-V_{x2})=(i_5'-i_5)R_{d5}+(i_5'-i_5)Z_5 \qquad (52)$$

$$(V_{x4}'-V_{x2}')-(V_{x4}-V_{x2})=(i_4'-i_4)R_{d4}+(i_4'-i_4)Z_4 \qquad (53)$$

$$(V_{x3}'-V_{x2}')-(V_{x3}-V_{x2})=(i_3'-i_3)R_{d3}+(i_3'-i_3)Z_3 \qquad (54)$$

$$(V_{x1}'-V_{x2}')-(V_{x1}-V_{x2})=(i_1'-i_1)R_{d1}+(i_1'-i_1)Z_1 \qquad (55)$$

$$(V_{x0}'-V_{x2}')-(V_{x0}-V_{x2})=(i_0'-i_0)R_{d0}+(i_0'-i_0)Z_0 \qquad (56)$$

Equations (52)-(56) can be rewritten as equations (57)-(61), where $\Delta V_{xj}=V_{xj}'-V_{xj}$ and $\Delta i_j=i_j'-i_j$.

$$\Delta V_{x5}-\Delta V_{x2}=\Delta i_5R_{d5}+\Delta i_5Z_5 \qquad (57)$$

$$\Delta V_{x4}-\Delta V_{x2}=\Delta i_4R_{d4}+\Delta i_4Z_4 \qquad (58)$$

$$\Delta V_{x3}-\Delta V_{x2}=\Delta i_3R_{d3}+\Delta i_3Z_3 \qquad (59)$$

$$\Delta V_{x1}-\Delta V_{x2}=\Delta i_1R_{d1}+\Delta i_1Z_1 \qquad (60)$$

$$\Delta V_{x0}-\Delta V_{x2}=\Delta i_0R_{d0}+\Delta i_0Z_0 \qquad (61)$$

In equations (57)-(61), $\Delta V_{xj}$ are based on measurements, $\Delta i_{xj}$ are controlled values, $R_{dj}$ are circuit constants, and $Z_j$ are unknowns that can be solved for based on the above systems of equations. If the measurement $V_{xj}'$ is done after the system is stabilized or settled, the resistance value, $R_j$ can be calculated:

$$R_j = Z_j = \frac{\Delta V_{xj} - \Delta V_{x2}}{\Delta i_j} - R_{dj} \qquad (62)$$

where $$j \neq 2$$

However, if one captures a sample before changing the current sources (e.g., the initial state described above), $V_{xj}(t=0^-)$, and three samples after changing the current source, $V_{xj}(t=1\,T_s,\,2\,T_s,\,3\,T_s)$, where $T_s$ is the time between samples, then the time constant $\tau_j=R_jC_j$, can be determined as discussed above relative to equations (1)-(26). This is because each $\Delta V_{xj}-\Delta V_{x2}$ (or other reference ECG electrode) is of the exponential function set forth in equation (1). There are multiple ways to solve for $\tau$, the description above is just one way in which this may be done.

Once $\tau_j$ and $R_j$ are determined, the capacitive component $C_j$ can be found from equation (63).

$$C_j = \frac{\tau_j}{R_j} \qquad (63)$$

Thus, the complete solution for the total impedance capacity including both resistive and capacitive components can be resolved from equation (64).

$$Z_j = \frac{R_j}{1 + sR_jC_j} \qquad (64)$$

The technique as disclosed to this point has determined the total contact impedance for each of the ECG electrodes $115_0$-$115_1$ and $115_3$-$115_5$. The total contact impedance for the ECG electrode $115_2$ has not yet been determined because it was selected as the first reference ECG electrode for the first pass. More particularly, as the reference ECG electrode, the injected current $i_2$ for the ECG electrode $115_2$ remained constant and was not changed. Since the technique determines the capacitive component of the contact impedance from the transition in the voltage as the injection current changes, and since there is no such transition in $V_{x2}$, the capacitive component of the contact impedance $Z_2$ cannot be found in the first pass.

Consequently, a second pass is made to determine $Z_2$. In this second pass, a second reference ECG electrode is selected. Since the point is to determine the contact impedance of the first reference ECG electrode, the second reference ECG electrode is different from the first reference ECG electrode. For purposes of illustration, this discussion will select ECG electrode $115_5$ as the second reference electrode for the second pass.

The injected currents $i_1'$-$i_4'$ are therefore changed again while, this time, the injected current $i_5'$ remains unchanged. The change to the injected currents $i_1'$-$i_4'$ needs to be significant enough to achieve a non-trivial change in $i_0'$. A non-trivial change, in this context, would be one sufficient large so that the transition from $V_{x0}'$ to $V_{x0}''$ yields good results in the determinations to follow. The nature and amount of this non-trivial change will be implementation specific in a manner that will become apparent to those skilled in the art having the benefit of this disclosure. However, in general $i_1$-$i_5$ should be set so that $i_0 \neq 0$.

Once the currents are changed, the value for T is again determined as discussed relative to FIG. 4 above. The process laid out relative to FIG. 5 above can then be repeated to determine $Z_2$ (including the capacitive component $C_2$) using $Z_5$ as the second reference. Note that this will result in a second set of equations based on new values for the quantities in Eqs. (27)-(64). Some embodiments may also repeat the process to determine $Z_0$-$Z_1$ and $Z_3$-$Z_4$ again. However, this is not necessary as these quantities have already been determined. At this point, each of $Z_0$-$Z_5$ has been determined, each determined $Z_0$-$Z_5$ including the capacitive component thereof.

Note that, as mentioned above, the presently disclosed embodiment determines the contact impedance $Z_j$ for each of six ECG electrodes. The technique may be readily adapted to any number of ECG electrodes given the disclosure presented herein. Thus, the technique is readily adaptable to, for instance, the 10 electrode, 12 lead configuration described above.

Accordingly, in at least one aspect, the presently disclosed technique includes the method 600 in FIG. 6. The method 600 may be performed by, for example, the processor-based control unit 121 of the ECG system 100 in FIG. 1. The method 600 may therefore be a software-implemented method in these embodiments.

The method 600 includes determining (at 605) a respective resistive component for each respective contact impedance of each respective ECG electrode of a plurality of monitored ECG electrodes (e.g., ECG electrodes $115_0$-$115_5$) ostensibly electrically connected to a human body (e.g., the body of patient 103) and determining (at 610) a respective capacitive component (e.g., $C_1$) for each respective contact impedance (e.g., $Z_1$-$Z_5$) of each respective ECG electrode. The presently disclosed embodiment determines the resistive component in the course of determining the capacitive component. However, this is not necessary in all embodiments. The resistive component may be determined (at 605) in any suitable manner known to the art. Furthermore, determining (at 605) the resistive component may also be determined either before or after the capacitive component is determined (at 610).

Determining (at 610) a respective capacitive component for each respective contact impedance begins, in this particular embodiment, by selecting (at 615) a first reference ECG electrode from among the plurality of ECG electrodes. The remainder of the ECG electrodes becoming non-reference ECG electrodes. In the example set forth above, the first reference ECG electrode is ECG electrode $115_2$ and ECG electrodes $115_0$-$115_1$ and $115_3$-$115_5$ are non-reference ECG electrodes.

Next, the respective contact impedance for each of the non-reference ECG electrodes is determined (at 620) from a first transition from a respective first ECG electrode voltage to a respective second ECG electrode voltage as a plurality of electrical currents driven through the ECG electrodes change, each respective contact impedance including a resistive component and a capacitive component. In the example above, the respective contact impedances are $Z_0$-$Z_1$ and $Z_3$-$Z_5$; the first ECG electrode voltages are $V_{x0}$-$V_{x1}$ and $V_{x3}$-$V_{x5}$; the second ECG electrode voltages are $V_{x0}'$-$V_{x1}'$ and $V_{x3}'$-$V_{x5}'$; and the driven electrical currents are $i_1$ and $i_3$-$i_5$ that change to $i_1'$ and $i_3'$-$i_5'$.

The method 600 then proceeds by selecting (at 625) a second reference ECG electrode from among the ECG electrodes, the second reference ECG electrode being different from the first reference ECG electrode, the rest of the ECG electrodes becoming second non-reference ECG electrodes. In the example described above, the second reference ECG electrode is ECG electrode $115_5$. Note that the second reference ECG electrode is different from the first so that the contact impedance of the first reference ECG electrode may be determined.

The method 600 then concludes by determining (at 630) the respective contact impedance for the non-reference ECG electrode previously identified as the first reference electrode from a second transition from a respective second ECG electrode voltage to a respective third ECG electrode voltage as the electrical currents driven through the ECG electrodes changes, the respective contact impedance including a resistive component and a capacitive component.

Returning to FIG. 1, once the complete contact impedance, including both resistive and capacitive components, is known for each of the ECG electrodes, the ECG electrodes can be used to more accurately monitor the ECG procedure 100. One particular embodiment uses the complete contact impedance to monitor for lead-off conditions as was discussed above. If a lead-off condition is detected, then an alarm can be sounded to alert nearby personnel that attention is needed. Table 2 sets forth monitored conditions for contact impedance and whether those conditions might lead to an alarm in one particular implementation.

TABLE 2

| Monitoring Conditions | | |
| --- | --- | --- |
| Resistive Component | Capacitive Component | Alarm |
| Low | Low | No |
| Low | High | No |
| High | Low | Yes |
| High | High | No |

Whether a determined resistive or capacitive component is "high" or "low" is determined by comparing the value thereof against a threshold. The value for the threshold may vary by implementation and embodiment as discussed above. However, on one particular embodiment, a high resistive component is one that is greater than 4MΩ and a low capacitive component is one that is less than 5 nF.

Accordingly, and still referring to FIG. 1, when the processor-based control unit 121 determines that the resistive component is high and the capacitive component is low for any particular ECG electrode 115, a signal is provided to the alarm generator 127. The alarm generator 127 then issues an alarm, whether aural, visual, or both. Note from Table 2 that the presently disclosed technique does not trigger a false alarm when the resistive component is high and the capacitive component is high. The presently disclosed technique is furthermore capable of distinguishing between that false alarm condition and a true alarm condition because the actual value of the capacitive component of the contact impedance is known. The presently disclosed technique may therefore forego lead-off false alarms that may be experienced in other, conventional ECG monitoring systems.

The foregoing outlines the features of several embodiments so that those of ordinary skill in the art may better understand various aspects of the present disclosure. Those of ordinary skill in the art should appreciate that they may readily use the present disclosure as a basis for designing or modifying other processes and structures for carrying out the same purposes and/or achieving the same advantages of various embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

Although the subject matter has been described in language specific to structural features or methodological acts, it is to be understood that the subject matter of the appended claims is not necessarily limited to the specific features or acts described above. Rather, the specific features and acts described above are disclosed as example forms of implementing at least some of the claims.

Various operations of embodiments are provided herein. The order in which some or all of the operations are described should not be construed to imply that these operations are necessarily order dependent. Alternative ordering will be appreciated having the benefit of this description. Further, it will be understood that not all operations are necessarily present in each embodiment provided herein. Also, it will be understood that not all operations are necessary in some embodiments.

It will be appreciated that layers, features, elements, etc., depicted herein are illustrated with particular dimensions relative to one another, such as structural dimensions or orientations, for example, for purposes of simplicity and ease of understanding and that actual dimensions of the same differ substantially from that illustrated herein, in some embodiments. Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application and the appended claims are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". Also, unless specified otherwise, "first," "second," or the like are not intended to imply a temporal aspect, a spatial aspect, an ordering, etc. Rather, such terms are merely used as identifiers, names, etc. for features, elements, items, etc. For example, a first element and a second element generally correspond to element A and element B or two different or two identical elements or the same element.

Accordingly, in a first embodiment, a method, comprises: monitoring a plurality of Electrocardiogram ("ECG") electrodes ostensibly electrically connected to a human body; determining the respective contact impedance for each of the ECG electrodes as a plurality of electrical currents is driven through the ECG electrodes in a predetermined pattern, each respective contact impedance including a resistive component and a capacitive component; ascertaining whether any of the determined respective contact impedances exceeds a predetermined threshold; and if any of the determined respective contact impedances exceeds the predetermined threshold, issuing an alarm.

In a second embodiment, monitoring the plurality of ECG electrodes in the first embodiment includes monitoring a plurality of ECG electrodes in a 10 electrode, 12 lead configuration or in a six electrode, six lead configuration.

In a third embodiment, determining the respective contact impedance for each of the ECG electrodes as a plurality of electrical currents is driven through the ECG electrodes in a predetermined pattern in the first embodiment includes: determining a respective resistive component for each respective contact impedance of each respective ECG electrode; and determining a respective capacitive component for each respective contact impedance of each respective ECG electrode. Determining the respective capacitive component for each respective contact impedance of each respective ECG electrode, includes: selecting a first reference ECG electrode from among the plurality of ECG electrodes, the remainder of the ECG electrodes becoming non-reference ECG electrodes; determining the respective contact impedance for each of the non-reference ECG electrodes from a first transition from a respective first ECG electrode voltage to a respective second ECG electrode voltage as a plurality of electrical currents driven through the ECG electrodes change, each respective contact impedance including a resistive component and a capacitive component; selecting a second reference ECG electrode from among the ECG electrodes, the second reference ECG electrode being different from the first reference ECG electrode, the rest of the ECG electrodes becoming second non-reference ECG electrodes; and determining the respective contact impedance for the non-reference ECG electrode previously identified as the first reference electrode from a second transition from a respective second ECG electrode voltage to a respective third ECG electrode voltage as the electrical currents driven through the ECG electrodes changes, the respective contact impedance including a resistive component and a capacitive component.

In a fourth embodiment, determining the respective resistive component for each respective contact impedance of each respective ECG electrode in the third embodiment is performed in the course of determining the respective capacitive component for each respective contact impedance of each respective ECG electrode.

In a fifth embodiment, determining the respective contact impedance for each of the ECG electrodes as a plurality of electrical currents is driven through the ECG electrodes in a predetermined pattern in the first embodiment includes: driving a first set of currents through the ECG electrodes to generate a first set of ECG electrode voltages, each current of the first set of currents having a respective first value, each current of the first set of currents being driven through a respective one of the ECG electrodes to generate a respective one of the first set of ECG electrode voltages; selecting a first reference ECG electrode from among the ECG electrodes, the rest of the ECG electrodes becoming non-reference ECG electrodes; driving a second set of currents through the non-reference ECG electrodes to generate a second set of ECG electrode voltages, the second set of currents having a second set of values different from the first set of currents, each respective current of the second set of currents being driven through a respective non-reference ECG electrode to generate a respective one of the second set of ECG voltages; driving a respective current from the first set of currents having a respective one of the first values through the first reference ECG electrode; determining the capacitive component of each respective contact impedance of each respective non-reference ECG electrode from the transition from the respective first ECG electrode voltage to the respective second ECG electrode voltage; selecting a second reference ECG electrode from among the ECG electrodes, the second reference ECG electrode being different from the first reference ECG electrode, the rest of the ECG electrodes becoming second non-reference ECG electrodes; driving a third set of currents through the second non-reference ECG electrodes to generate a third set of ECG electrode voltages, the third set of currents having a third set of values different from the second set of currents, each respective current of the third set of currents being driven through a respective second non-reference ECG electrode to generate a respective one of the third set of ECG voltages while a respective current, from the second set of currents is driven through the second reference ECG electrode; determining the capacitive component of the respective contact impedance of the first reference ECG electrode from the transition from the respective second ECG electrode voltage to the respective third ECG electrode voltage; and determining the respective resistive component of the respective contact impedance for each of the ECG electrodes.

In a sixth embodiment, determining the respective contact impedance for each of the ECG electrodes as a plurality of electrical currents is driven through the ECG electrodes in a predetermined pattern in the first embodiment includes: driving a first current through each of the ECG electrodes; selecting a first reference ECG electrode from among the plurality of ECG electrodes; while driving the first current through the first reference ECG electrode, driving a second current through the rest of the ECG electrodes, the second current having a different value than the first; determining the capacitive component of the contact impedance for each of the ECG electrodes excepting the first reference ECG electrode; selecting a second reference ECG electrode from among the ECG electrodes, the second reference ECG electrode being different from the first reference ECG electrode; while driving the second current through the second reference ECG electrode, driving a third current through the rest of the ECG electrodes, the third current having a different value than the second; determining the capacitive component of the contact impedance for the first reference ECG electrode; and determining the respective resistive component of each respective contact impedance for each respective ECG electrode.

In a seventh embodiment, issuing the alarm in the first embodiment includes: sounding an audio alarm; or presenting a visual alarm; or a combination of sounding the audio alarm and presenting the visual alarm.

In an eighth embodiment, an Electrocardiogram ("ECG") system, comprises;

a plurality of ECG electrodes; a plurality of electrical leads; and an ECG monitor electrically connected to the ECG electrodes by the electrical leads. The ECG monitor includes: a sensor interface through which the ECG monitor receives signals from and sends signals to the ECG electrodes; and a processor-based control unit. The processor-based control unit is programmed to, through the sensor interface: monitor the ECG electrodes when the ECG electrodes are ostensibly electrically connected to a human body; determine the respective contact impedance for each of the ECG electrodes as a plurality of electrical currents is driven through the ECG electrodes in a predetermined pattern, each respective contact impedance including a resistive component and a capacitive component; ascertain whether any of the determined respective contact impedances exceeds a predetermined threshold; and if any of the determined respective contact impedances exceeds the predetermined threshold, issuing an alarm.

In a ninth embodiment, the ECG electrodes and the leads of the eight embodiment are arranged in a 10 electrode, 12 lead configuration or in a six electrode, six lead configuration.

In a tenth embodiment, determining the respective contact impedance for each of the EGG electrodes as a plurality of electrical currents is driven through the ECG electrodes in a predetermined pattern in the eighth embodiment includes: determining a respective resistive component for each respective contact impedance of each respective ECG electrode; and determining a respective capacitive component for each respective contact impedance of each respective ECG electrode. Determining the respective capacitive component for each respective contact impedance of each respective ECG electrode includes: selecting a first reference ECG electrode from among the plurality of EGG electrodes, the remainder of the ECG electrodes becoming non-reference ECG electrodes; determining the respective contact impedance for each of the non-reference ECG electrodes from a first transition from a respective first ECG electrode voltage to a respective second ECG electrode voltage as a plurality of electrical currents driven through the ECG electrodes change, each respective contact impedance including a resistive component and a capacitive component; selecting a second reference ECG electrode from among the ECG electrodes, the second reference ECG electrode being different from the first reference ECG electrode, the rest of the ECG electrodes becoming second non-reference ECG electrodes; and determining the respective contact impedance for the non-reference ECG electrode previously identified as the first reference electrode from a second transition from a respective second ECG electrode voltage to a respective third ECG electrode voltage as the electrical currents driven through the ECG electrodes changes, the respective contact impedance including a resistive component and a capacitive component.

In an eleventh embodiment, determining the respective resistive component for each respective contact impedance of each respective ECG electrode in the tenth embodiment is performed in the course of determining the respective capacitive component for each respective contact impedance of each respective ECG electrode.

In a twelfth embodiment, determining the respective contact impedance for each of the ECG electrodes as a plurality of electrical currents is driven through the ECG electrodes in a predetermined pattern in the eight embodiment includes: driving a first set of currents through the ECG electrodes to generate a first set of ECG electrode voltages, each current of the first set of currents having a respective first value, each current of the first set of currents being driven through a respective one of the ECG electrodes to generate a respective one of the first set of ECG electrode voltages; selecting a first reference ECG electrode from among the ECG electrodes, the rest of the ECG electrodes becoming non-reference ECG electrodes; driving a second set of currents through the non-reference ECG electrodes to generate a second set of ECG electrode voltages, the second set of currents having a second set of values different from the first set of currents, each respective current of the second set of currents being driven through a respective non-reference ECG electrode to generate a respective one of the second set of ECG voltages; driving a respective current from the first set of currents having a respective one of the first values through the first reference ECG electrode; determining the capacitive component of each respective contact impedance of each respective non-reference ECG electrode from the transition from the respective first ECG electrode voltage to the respective second ECG electrode voltage; selecting a second reference ECG electrode from among the ECG electrodes, the second reference ECG electrode being different from the first reference ECG electrode, the rest of the ECG electrodes becoming second non-reference ECG electrodes; driving a third set of currents through the second non-reference ECG electrodes to generate a third set of ECG electrode voltages, the third set of currents having a third set of values different from the second set of currents, each respective current of the third set of currents being driven through a respective second non-reference ECG electrode to generate a respective one of the third set of ECG voltages while a respective current, from the second set of currents is driven through the second reference ECG electrode; determining the capacitive component of the respective contact impedance of the first reference ECG electrode from the transition from the respective second EGG electrode voltage to the respective third ECG electrode voltage; and determining the respective resistive component of the respective contact impedance for each of the ECG electrodes.

In a thirteenth embodiment, wherein determining the respective contact impedance for each of the ECG electrodes as a plurality of electrical currents is driven through the ECG electrodes in a predetermined pattern in the eighth embodiment includes: driving a first current through each of the ECG electrodes; selecting a first reference ECG electrode from among the plurality of ECG electrodes; while driving the first current through the first reference ECG electrode, driving a second current through the rest of the ECG electrodes, the second current having a different value than the first; determining the capacitive component of the contact impedance for each of the ECG electrodes excepting the first reference ECG electrode; selecting a second reference ECG electrode from among the ECG electrodes, the second reference ECG electrode being different from the first reference ECG electrode; while driving the second current through the second reference ECG electrode, driving a third current through the rest of the ECG electrodes, the third current having a different value than the second; determining the capacitive component of the contact impedance for the first reference ECG electrode; and determining the respective resistive component of each respective contact impedance for each respective ECG electrode.

In a fourteenth embodiment, the eighth embodiment further comprises an alarm generator to sound an audio alarm or present a visual alarm.

In a fifteenth embodiment, the eighth embodiment further comprises a display.

In a sixteenth embodiment, the display of the fifteenth embodiment: presents at least a portion of a user interface when the ECG system is in use; or presents a visual alarm when the alarm is issued; or both presents at least the portion of the user interface when the ECG system is in use and presents the visual alarm when the alarm is issued.

In a seventeenth embodiment, a computer readable medium encoded with instructions that, when executed by a processor, perform a method comprising: monitoring a plurality of Electrocardiogram ("ECG") electrodes ostensibly electrically connected to a human body; driving a plurality of electrical currents through the monitored ECG electrodes in a predetermined pattern; determining the respective contact impedance for each of the ECG electrodes as the electrical currents are driven through the ECG electrodes in the predetermined pattern, each respective contact impedance including a resistive component and a capacitive component; and ascertaining whether any of the determined respective contact impedances exceeds a predetermined threshold; and if any of the determined respective contact impedances exceeds the predetermined threshold exceeds the predetermined threshold, issuing an alarm.

In an eighteenth embodiment, monitoring the plurality of ECG electrodes in the method in the seventeenth embodiment includes monitoring a plurality of ECG electrodes in a 10 electrode, 12 lead configuration or in a six electrode, six lead configuration.

In a nineteenth embodiment, determining the respective contact impedance for each of the ECG electrodes as a plurality of electrical currents is driven through the ECG electrodes in a predetermined pattern in the seventeenth embodiment includes: determining a respective resistive component for each respective contact impedance of each respective ECG electrode; and determining a respective capacitive component for each respective contact impedance of each respective ECG electrode. Determining a respective capacitive component for each respective contact impedance of each respective ECG electrode includes: selecting a first reference ECG electrode from among the plurality of ECG electrodes, the remainder of the ECG electrodes becoming non-reference ECG electrodes; determining the respective contact impedance for each of the non-reference ECG electrodes from a first transition from a respective first ECG electrode voltage to a respective second ECG electrode voltage as a plurality of electrical currents driven through the ECG electrodes change, each respective contact impedance including a resistive component and a capacitive component; selecting a second reference ECG electrode from among the ECG electrodes, the second reference ECG electrode being different from the first reference EGG electrode, the rest of the ECG electrodes becoming second non-reference ECG electrodes; and determining the respective contact impedance for the non-reference ECG electrode previously identified as the first reference electrode from a second transition from a respective second ECG electrode voltage to a respective third ECG electrode voltage as the electrical currents driven through the EGG electrodes changes, the respective contact impedance including a resistive component and a capacitive component.

In a twentieth embodiment, determining the respective resistive component for each respective contact impedance of each respective ECG electrode in the nineteenth embodiment is performed in the course of determining the respective capacitive component for each respective contact impedance of each respective ECG electrode.

In a twenty-first embodiment, determining the respective contact impedance for each of the ECG electrodes as a plurality of electrical currents is driven through the ECG electrodes in a predetermined pattern in the seventeenth embodiment includes: driving a first set of currents through the ECG electrodes to generate a first set of ECG electrode voltages, each current of the first set of currents having a respective first value, each current of the first set of currents being driven through a respective one of the ECG electrodes to generate a respective one of the first set of ECG electrode voltages; selecting a first reference ECG electrode from among the ECG electrodes, the rest of the ECG electrodes becoming non-reference ECG electrodes; driving a second set of currents through the non-reference ECG electrodes to generate a second set of ECG electrode voltages, the second set of currents having a second set of values different from the first set of currents, each respective current of the second set of currents being driven through a respective non-reference ECG electrode to generate a respective one of the second set of ECG voltages; driving a respective current from the first set of currents having a respective one of the first values through the first reference ECG electrode; determining the capacitive component of each respective contact impedance of each respective non-reference ECG electrode from the transition from the respective first ECG electrode voltage to the respective second ECG electrode voltage; selecting a second reference ECG electrode from among the ECG electrodes, the second reference ECG electrode being different from the first reference ECG electrode, the rest of the ECG electrodes becoming second non-reference ECG electrodes; driving a third set of currents through the second non-reference ECG electrodes to generate a third set of ECG electrode voltages, the third set of currents having a third set of values different from the second set of currents, each respective current of the third set of currents being driven through a respective second non-reference ECG electrode to generate a respective one of the third set of ECG voltages while a respective current, from the second set of currents is driven through the second reference ECG electrode; determining the capacitive component of the respective contact impedance of the first reference ECG electrode from the transition from the respective second ECG electrode voltage to the respective third ECG electrode voltage; and determining the respective resistive component of the respective contact impedance for each of the ECG electrodes.

In a twenty-second embodiment, determining the respective contact impedance for each of the ECG electrodes as a plurality of electrical currents is driven through the ECG electrodes in a predetermined pattern in the seventeenth embodiment includes: driving a first current through each of the ECG electrodes; selecting a first reference ECG electrode from among the plurality of ECG electrodes; while driving the first current through the first reference ECG electrode, driving a second current through the rest of the ECG electrodes, the second current having a different value than the first; determining the capacitive component of the contact impedance for each of the ECG electrodes excepting the first reference ECG electrode; selecting a second reference ECG electrode from among the ECG electrodes, the second reference ECG electrode being different from the first reference ECG electrode; while driving the second current through the second reference ECG electrode, driving a third current through the rest of the ECG electrodes, the third current having a different value than the second; determining the capacitive component of the contact impedance for the first reference ECG electrode; and determining the respective resistive component of each respective contact impedance for each respective ECG electrode.

In a twenty-third embodiment, issuing the alarm in the seventeenth embodiments includes: sounding an audio alarm; or presenting a visual alarm; or a combination of sounding the audio alarm and presenting the visual alarm.

In a twenty-fourth embodiment, a method comprises: determining a respective resistive component for each respective contact impedance of each respective Electrocardiogram ("ECG") electrode of a plurality of monitored ECG electrodes ostensibly electrically connected to a human body; and determining a respective capacitive component for each respective contact impedance of each respective ECG electrode. Determining a respective capacitive component for each respective contact impedance of each respective ECG electrode includes: selecting a first reference ECG electrode from among the plurality of ECG electrodes, the remainder of the ECG electrodes becoming non-reference ECG electrodes; determining the respective contact impedance for each of the non-reference EGG electrodes from a first transition from a respective first ECG electrode voltage to a respective second ECG electrode voltage as a plurality of electrical currents driven through the ECG electrodes change, each respective contact impedance including a resistive component and a capacitive component; selecting a second reference ECG electrode from among the ECG electrodes, the second reference ECG electrode being different from the first reference ECG electrode, the rest of the ECG electrodes becoming second non-reference ECG electrodes; and determining the respective contact impedance for the non-reference ECG electrode previously identified as the first reference electrode from a second transition from a respective second ECG electrode voltage to a respective third ECG electrode voltage as the electrical currents driven through the ECG electrodes changes, the respective contact impedance including a resistive component and a capacitive component.

In a twenty-fifth embodiment, the twenty-fourth embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a twenty-sixth embodiment, in the method of the twenty-fourth embodiment, wherein determining the respective resistive component for each respective contact impedance of each respective ECG electrode is performed in the course of determining the respective capacitive component for each respective contact impedance of each respective ECG electrode.

In a twenty-seventh embodiment, the plurality of ECG electrodes in the twenty-fourth embodiment includes six electrodes or 10 electrodes.

In a twenty-eighth embodiment, an electrocardiogram ("ECG") system comprises: a plurality of ECG electrodes; a plurality of electrical leads; and an ECG monitor electrically connected to the ECG electrodes by the electrical leads. The ECG monitor includes a sensor interface through which the ECG monitor receives signals from and sends signals to the ECG electrodes; and a processor-based control unit. The processor-based control unit is programmed to, through the sensor interface: determining a respective resistive component for each respective contact impedance of each respective ECG electrode of a plurality of monitored ECG electrodes ostensibly electrically connected to a human body; and determining a respective capacitive component for each respective contact impedance of each respective ECG electrode. Determining a respective capacitive component for each respective contact impedance of each respective ECG electrode includes: selecting a first reference ECG electrode from among the plurality of ECG electrodes, the remainder of the ECG electrodes becoming non-reference ECG electrodes; determining the respective contact impedance for each of the non-reference ECG electrodes from a first transition from a respective first ECG electrode voltage to a respective second ECG electrode voltage as a plurality of electrical currents driven through the ECG electrodes change, each respective contact impedance including a resistive component and a capacitive component; selecting a second reference ECG electrode from among the ECG electrodes, the second reference ECG electrode being different from the first reference ECG electrode, the rest of the ECG electrodes becoming second non-reference ECG electrodes; and determining the respective contact impedance for the non-reference ECG electrode previously identified as the first reference electrode from a second transition from a respective second ECG electrode voltage to a respective third ECG electrode voltage as the electrical currents driven through the EGG electrodes changes, the respective contact impedance including a resistive component and a capacitive component.

In a twenty-ninth embodiment, the twenty-eighth embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a thirtieth embodiment, determining the respective resistive component for each respective contact impedance of each respective ECG electrode in the twenty-eighth embodiment is performed in the course of determining the respective capacitive component for each respective contact impedance of each respective ECG electrode.

In a thirty-first embodiment, the ECG electrodes and the leads in the twenty-eighth embodiment are arranged in a 10 electrode, 12 lead configuration or in a six electrode, six lead configuration.

In a thirty-second embodiment, the twenty-eighth embodiment further comprises an alarm generator to sound an audio alarm or present a visual alarm.

In a thirty-third embodiment, the twenty-eighth embodiment further comprises a display.

In a thirty-fourth embodiment, the display in the thirty-third embodiment: presents at least a portion of a user interface when the ECG system is in use; or presents a visual alarm when the alarm is issued; or both presents at least the portion of the user interface when the ECG system is in use and presents the visual alarm when the alarm is issued.

In a thirty-fifth embodiment, a computer readable medium is encoded with instructions that, when executed by a processor, perform a method comprising: determining a respective resistive component for each respective contact impedance of each respective Electrocardiogram ("ECG") electrode of a plurality of monitored ECG electrodes ostensibly electrically connected to a human body; and determining a respective capacitive component for each respective contact impedance of each respective ECG electrode. Determining a respective capacitive component for each respective contact impedance of each respective ECG electrode includes: selecting a first reference ECG electrode from among the plurality of ECG electrodes, the remainder of the ECG electrodes becoming non-reference ECG electrodes; determining the respective contact impedance for each of the non-reference ECG electrodes from a first transition from a respective first ECG electrode voltage to a respective second ECG electrode voltage as a plurality of electrical currents driven through the ECG electrodes change, each respective contact impedance including a resistive component and a capacitive component; selecting a second reference ECG electrode from among the ECG electrodes, the second reference ECG electrode being different from the first reference ECG electrode, the rest of the ECG electrodes becoming second non-reference ECG electrodes; and determining the respective contact impedance for the non-reference ECG electrode previously identified as the first reference electrode from a second transition from a respective second ECG electrode voltage to a respective third ECG electrode voltage as the electrical currents driven through the ECG electrodes changes, the respective contact impedance including a resistive component and a capacitive component.

In a thirty-sixth embodiment, the method of the thirty-fifth embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a thirty-seventh embodiment, determining the respective resistive component for each respective contact impedance of each respective ECG electrode in the thirty-fifth embodiment is performed in the course of determining the respective capacitive component for each respective contact impedance of each respective ECG electrode.

In a thirty-eighth embodiment, monitoring the plurality of ECG electrodes in the thirty-fifth embodiment includes monitoring a plurality of ECG electrodes in a 10 electrode, 12 lead configuration or in a six electrode, six lead configuration.

In a thirty-ninth embodiment, a method, comprises: monitoring a plurality of Electrocardiogram ("ECG") electrodes ostensibly electrically connected to a human body; driving a first set of currents through the ECG electrodes to generate a first set of ECG electrode voltages, each current of the first set of currents having a respective first value, each current of the first set of currents being driven through a respective one of the ECG electrodes to generate a respective one of the first set of ECG electrode voltages; selecting a first reference ECG electrode from among the ECG electrodes, the rest of the ECG electrodes becoming non-reference ECG electrodes; driving a second set of currents through the non-reference ECG electrodes to generate a second set of ECG electrode voltages, the second set of currents having a second set of values different from the first set of currents, each respective current of the second set of currents being driven through a respective non-reference ECG electrode to generate a respective one of the second set of ECG voltages; driving a respective current from the first set of currents having a respective one of the first values through the first reference ECG electrode; determining the capacitive component of each respective contact impedance of each respective non-reference ECG electrode from the transition from the respective first ECG electrode voltage to the respective second ECG electrode voltage; selecting a second reference ECG electrode from among the ECG electrodes, the second reference ECG electrode being different from the first reference ECG electrode, the rest of the ECG electrodes becoming second non-reference ECG electrodes; driving a third set of currents through the second non-reference ECG electrodes to generate a third set of ECG electrode voltages, the third set of currents having a third set of values different from the second set of currents, each respective current of the third set of currents being driven through a respective second non-reference ECG electrode to generate a respective one of the third set of ECG voltages while a respective current, from the second set of currents is driven through the second reference ECG electrode; determining the capacitive component of the respective contact impedance of the first reference ECG electrode from the transition from the respective second ECG electrode voltage to the respective third ECG electrode voltage; and determining the respective resistive component of the respective contact impedance for each of the ECG electrodes.

In a fortieth embodiment, the thirty-ninth embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a forty-first embodiment, monitoring the plurality of ECG electrodes in the thirty-ninth embodiment includes monitoring a plurality of ECG electrodes in a 10 electrode, 12 lead configuration or in a six electrode, six lead configuration.

In a forty-second embodiment, determining the respective resistive component for each respective contact impedance of each respective ECG electrode in the thirty-ninth embodiment is performed in the course of determining the respective capacitive component for each respective contact impedance of each respective ECG electrode.

In a forty-third embodiment, issuing the alarm in the thirty-ninth embodiment includes: sounding an audio alarm; or presenting a visual alarm; or a combination of sounding the audio alarm and presenting the visual alarm.

In a forty-fourth embodiment, An Electrocardiogram ("ECG") system, comprising: a plurality of ECG electrodes; a plurality of electrical leads; and an ECG monitor electrically connected to the ECG electrodes by the electrical leads, the ECG monitor. The ECG monitor includes: a sensor interface through which the ECG monitor receives signals from and sends signals to the ECG electrodes; and a processor-based control unit. The processor-based control unit is programmed to, through the sensor interface: monitor a plurality of Electrocardiogram ("ECG") electrodes ostensibly electrically connected to a human body when the ECG monitor is in use; drive a first set of currents through the ECG electrodes to generate a first set of ECG electrode voltages, each current of the first set of currents having a respective first value, each current of the first set of currents being driven through a respective one of the ECG electrodes to generate a respective one of the first set of ECG electrode voltages; select a first reference ECG electrode from among the EGG electrodes, the rest of the ECG electrodes becoming non-reference ECG electrodes; drive a second set of currents through the non-reference ECG electrodes to generate a second set of ECG electrode voltages, the second set of currents having a second set of values different from the first set of currents, each respective current of the second set of currents being driven through a respective non-reference ECG electrode to generate a respective one of the second set of ECG voltages; drive a respective current from the first set of currents having a respective one of the first values through the first reference ECG electrode; determine the capacitive component of each respective contact impedance of each respective non-reference ECG electrode from the transition from the respective first ECG electrode voltage to the respective second ECG electrode voltage; select a second reference ECG electrode from among the ECG electrodes, the second reference ECG electrode being different from the first reference ECG electrode, the rest of the ECG electrodes becoming second non-reference ECG electrodes; drive a third set of currents through the second non-reference ECG electrodes to generate a third set of ECG electrode voltages, the third set of currents having a third set of values different from the second set of currents, each respective current of the third set of currents being driven through a respective second non-reference ECG electrode to generate a respective one of the third set of ECG voltages while a respective current, from the second set of currents is driven through the second reference ECG electrode; determine the capacitive component of the respective contact impedance of the first reference ECG electrode from the transition from the respective second ECG electrode voltage to the respective third ECG electrode voltage; and determine the respective resistive component of the respective contact impedance for each of the ECG electrodes.

In a forty-fifth embodiment, the forty-fourth embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a forty-sixth embodiment, monitoring the plurality of ECG electrodes in the forty-fourth embodiment includes monitoring a plurality of ECG electrodes in a 10 electrode, 12 lead configuration or in a six electrode, six lead configuration.

In a forty-seventh embodiment, determining the respective resistive component for each respective contact impedance of each respective ECG electrode in the forty-fourth embodiment is performed in the course of determining the respective capacitive component for each respective contact impedance of each respective ECG electrode.

In a forty-eighth embodiment, issuing the alarm in the forty-fourth embodiment includes: sounding an audio alarm; or presenting a visual alarm; or a combination of sounding the audio alarm and presenting the visual alarm.

In a forty-ninth embodiment, the forty-fourth embodiment further comprises a display.

In a fiftieth embodiment, the display of the forty-ninth embodiment: presents at least a portion of a user interface when the ECG system is in use; or presents a visual alarm when the alarm is issued; or both presents at least the portion of the user interface when the ECG system is in use and presents the visual alarm when the alarm is issued.

In a fifty-first embodiment, computer readable medium is encoded with instructions that, when executed by a processor, perform a method comprising: monitoring a plurality of Electrocardiogram ("ECG") electrodes ostensibly electrically connected to a human body; driving a first set of currents through the ECG electrodes to generate a first set of ECG electrode voltages, each current of the first set of currents having a respective first value, each current of the first set of currents being driven through a respective one of the ECG electrodes to generate a respective one of the first set of ECG electrode voltages; selecting a first reference ECG electrode from among the ECG electrodes, the rest of the ECG electrodes becoming non-reference ECG electrodes; driving a second set of currents through the non-reference ECG electrodes to generate a second set of ECG electrode voltages, the second set of currents having a second set of values different from the first set of currents, each respective current of the second set of currents being driven through a respective non-reference ECG electrode to generate a respective one of the second set of ECG voltages; driving a respective current from the first set of currents having a respective one of the first values through the first reference ECG electrode; determining the capacitive component of each respective contact impedance of each respective non-reference ECG electrode from the transition from the respective first ECG electrode voltage to the respective second ECG electrode voltage; selecting a second reference ECG electrode from among the ECG electrodes, the second reference ECG electrode being different from the first reference ECG electrode, the rest of the ECG electrodes becoming second non-reference ECG electrodes; driving a third set of currents through the second non-reference ECG electrodes to generate a third set of ECG electrode voltages, the third set of currents having a third set of values different from the second set of currents, each respective current of the third set of currents being driven through a respective second non-reference ECG electrode to generate a respective one of the third set of ECG voltages while a respective current, from the second set of currents is driven through the second reference ECG electrode; determining the capacitive component of the respective contact impedance of the first reference ECG electrode from the transition from the respective second ECG electrode voltage to the respective third ECG electrode voltage; and determining the respective resistive component of the respective contact impedance for each of the ECG electrodes.

In a fifty-second embodiment, wherein the fifty-first embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a fifty-third embodiment, monitoring the plurality of ECG electrodes in the fifty-first embodiment includes monitoring a plurality of ECG electrodes in a 10 electrode, 12 lead configuration or in a six electrode, six lead configuration.

In a fifty-fourth embodiment, in the computer readable medium of the forty-second embodiment, wherein determining the respective resistive component for each respective contact impedance of each respective ECG electrode is performed in the course of determining the respective capacitive component for each respective contact impedance of each respective ECG electrode.

In a fifty-fifth embodiment, issuing the alarm on the fifty-first embodiment includes: sounding an audio alarm; or presenting a visual alarm; or a combination of sounding the audio alarm and presenting the visual alarm.

In a fifty-sixth embodiment, a method, comprises: monitoring a plurality of Electrocardiogram ("ECG") electrodes ostensibly electrically connected to a human body; driving a first current through each of the ECG electrodes; selecting a first reference ECG electrode from among the plurality of ECG electrodes; while driving the first current through the first reference ECG electrode, driving a second current through the rest of the EGG electrodes, the second current having a different value than the first; determining the capacitive component of the contact impedance for each of the ECG electrodes excepting the first reference ECG electrode; selecting a second reference ECG electrode from among the ECG electrodes, the second reference ECG electrode being different from the first reference ECG electrode; while driving the second current through the second reference ECG electrode, driving a third current through the rest of the ECG electrodes, the third current having a different value than the second; determining the capacitive component of the contact impedance for the first reference ECG electrode; and determining the respective resistive component of each respective contact impedance for each respective ECG electrode.

In a fifty-seventh embodiment, the fifty-sixth embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a fifty-eighth embodiment, issuing the alarm in the fifty-seventh embodiment includes: sounding an audio alarm; or presenting a visual alarm; or a combination of sounding the audio alarm and presenting the visual alarm.

In a fifty-ninth embodiment, monitoring the plurality of ECG electrodes in the fifty-sixth embodiment includes monitoring a plurality of ECG electrodes in a 10 electrode, 12 lead configuration or in a six electrode, six lead configuration.

In a sixtieth embodiment, determining the respective resistive component for each respective contact impedance of each respective ECG electrode in the fifty-sixth embodiment is performed in the course of determining the respective capacitive component for each respective contact impedance of each respective ECG electrode.

In a sixty-first embodiment, an Electrocardiogram ("ECG") system, comprises: a plurality of ECG electrodes; a plurality of electrical leads; and an ECG monitor electrically connected to the ECG electrodes by the electrical leads. The ECG monitor includes: a sensor interface through which the ECG monitor receives signals from and sends signals to the ECG electrodes; and a processor-based control unit. The processor-based control unit is programmed to, through the sensor interface: monitor a plurality of Electrocardiogram ("ECG") electrodes ostensibly electrically connected to a human body; drive a first current through each of the ECG electrodes; select a first reference ECG electrode from among the plurality of ECG electrodes; while driving the first current through the first reference ECG electrode, drive a second current through the rest of the ECG electrodes, the second current having a different value than the first; determine the capacitive component of the contact impedance for each of the ECG electrodes excepting the first reference ECG electrode; select a second reference ECG electrode from among the ECG electrodes, the second reference ECG electrode being different from the first reference ECG electrode; while driving the second current through the second reference ECG electrode, drive a third current through the rest of the ECG electrodes, the third current having a different value than the second; determine the capacitive component of the contact impedance for the first reference ECG electrode; and determine the respective resistive component of each respective contact impedance for each respective ECG electrode.

In a sixty-second embodiment, the sixty-first embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a sixty-third embodiment, issuing the alarm in the sixty-second embodiment includes: sounding an audio alarm; or presenting a visual alarm; or a combination of sounding the audio alarm and presenting the visual alarm.

In a sixty-fourth embodiment, determining the respective resistive component for each respective contact impedance of each respective ECG electrode in the sixty-first embodiment is performed in the course of determining the respective capacitive component for each respective contact impedance of each respective ECG electrode.

In a sixty-fifth embodiment, monitoring the plurality of ECG electrodes in the sixty-first embodiment includes monitoring a plurality of ECG electrodes in a 10 electrode, 12 lead configuration or in a six electrode, six lead configuration.

In a sixty-sixth embodiment, a computer readable medium is encoded with instructions that, when executed by a processor, perform a method comprising: monitoring a plurality of Electrocardiogram ("ECG") electrodes ostensibly electrically connected to a human body; driving a first current through each of the ECG electrodes; selecting a first reference ECG electrode from among the plurality of ECG electrodes; while driving the first current through the first reference ECG electrode, driving a second current through the rest of the ECG electrodes, the second current having a different value than the first; determining the capacitive component of the contact impedance for each of the ECG electrodes excepting the first reference ECG electrode; selecting a second reference ECG electrode from among the ECG electrodes, the second reference ECG electrode being different from the first reference ECG electrode; while driving the second current through the second reference ECG electrode, driving a third current through the rest of the ECG electrodes, the third current having a different value than the second; determining the capacitive component of the contact impedance for the first reference ECG electrode; and determining the respective resistive component of each respective contact impedance for each respective ECG electrode.

In a sixty-seventh embodiment, the sixty-sixth embodiment further comprises: ascertaining whether any of the determined respective contact impedances exceeds a predetermined threshold; and if any of the determined respective contact impedances exceeds the predetermined threshold exceeds the predetermined threshold, issuing an alarm.

In a sixty-eighth embodiment, issuing the alarm in the sixty-seventh embodiment includes: sounding an audio alarm; or presenting a visual alarm; or a combination of sounding the audio alarm and presenting the visual alarm.

In a sixty-ninth embodiment, monitoring the plurality of ECG electrodes in the sixty-sixth embodiment includes monitoring a plurality of ECG electrodes in a 10 electrode, 12 lead configuration or in a six electrode, six lead configuration.

In a seventieth embodiment, determining the respective resistive component for each respective contact impedance of each respective ECG electrode in the sixty-sixth embodiment is performed in the course of determining the respective capacitive component for each respective contact impedance of each respective ECG electrode.

This concludes the detailed description. The particular examples disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular examples disclosed above may be altered or modified and all such variations are considered within the scope and spirit of the invention. Accordingly, the protection sought herein is as set forth in the claims below.

What is claimed is:

1. A method, comprising:
monitoring a plurality of Electrocardiogram ("ECG") electrodes ostensibly electrically connected to a human body;
driving a plurality of electrical currents through the ECG electrodes in a predetermined pattern;
determining a respective contact impedance for each of the ECG electrodes as the plurality of electrical currents is driven through the ECG electrodes in the predetermined pattern, each respective contact impedance including a resistive component and a capacitive component, including determining the respective resistive component and the respective capacitive component for each respective contact impedance of each respective ECG electrode, the determining including:
selecting a first reference ECG electrode from among the plurality of ECG electrodes, the remainder of the ECG electrodes becoming non-reference ECG electrodes;
determining the respective contact impedance for each of the non-reference ECG electrodes from a first transition from a respective first ECG electrode voltage to a respective second ECG electrode voltage as the plurality of electrical currents driven through the ECG electrodes change, each respective contact impedance including a resistive component and a capacitive component;
selecting a second reference ECG electrode from among the ECG electrodes, the second reference ECG electrode being different from the first reference ECG electrode, the rest of the ECG electrodes becoming second non-reference ECG electrodes; and
determining the respective contact impedance for the non-reference ECG electrode previously identified as the first reference electrode from a second transition from a respective second ECG electrode voltage to a respective third ECG electrode voltage as the electrical currents driven through the ECG electrodes changes, the respective contact impedance including the resistive component and the capacitive component;
ascertaining whether any of the determined respective contact impedances exceeds a predetermined threshold;
when any of the determined respective contact impedances exceeds the predetermined threshold, issuing a lead-off alarm.

2. The method of claim 1, wherein monitoring the plurality of ECG electrodes includes monitoring a plurality of ECG electrodes in a 10 electrode, 12 lead configuration or in a six electrode, six lead configuration.

3. The method of claim 1, wherein determining the respective resistive component for each respective contact impedance of each respective ECG electrode is performed in the course of determining the respective capacitive component for each respective contact impedance of each respective ECG electrode.

4. The method of claim 1, wherein issuing the alarm includes:
sounding an audio alarm; or
presenting a visual alarm; or
a combination of sounding the audio alarm and presenting the visual alarm.

5. An Electrocardiogram ("ECG") system, comprising:
a plurality of ECG electrodes;
a plurality of electrical leads; and
an ECG monitor electrically connected to the ECG electrodes by the electrical leads, the ECG monitor including:
a sensor interface through which the ECG monitor receives signals from and sends signals to the ECG electrodes; and
a processor-based control unit programmed to, through the sensor interface:
monitor the ECG electrodes when the ECG electrodes are ostensibly electrically connected to a human body;
drive a plurality of electrical currents through the ECG electrodes in a predetermined pattern;
determine a respective contact impedance for each of the ECG electrodes as the plurality of electrical currents is driven through the ECG electrodes in the predetermined pattern, each respective contact impedance including a resistive component and a capacitive component, including determining the respective resistive component and the respective capacitive component for each respective contact impedance of each respective ECG electrode, the determining including:
selecting a first reference ECG electrode from among the plurality of ECG electrodes, the remainder of the ECG electrodes becoming non-reference ECG electrodes;
determining the respective contact impedance for each of the non-reference ECG electrodes from a first transition from a respective first ECG electrode voltage to a respective second ECG electrode voltage as the plurality of electrical currents driven through the ECG electrodes change, each respective contact impedance including a resistive component and a capacitive component;
selecting a second reference ECG electrode from among the ECG electrodes, the second reference ECG electrode being different from the first reference ECG electrode, the rest of the ECG electrodes becoming second non-reference ECG electrodes; and determining the respective contact impedance for the non-reference ECG electrode previously identified as the first reference electrode from a second transition from a respective second ECG electrode voltage to a respective third ECG electrode voltage as the electrical currents driven through the ECG electrodes changes, the respective contact impedance including a resistive component and a capacitive component;

ascertain whether any of the determined respective contact impedances exceeds a predetermined threshold;

when any of the determined respective contact impedances exceeds the predetermined threshold, issue a lead-off alarm.

6. The ECG system of claim 5, wherein the ECG electrodes and the leads are arranged in a 10 electrode, 12 lead configuration or in a six electrode, six lead configuration.

7. The ECG system of claim 5, wherein determining the respective resistive component for each respective contact impedance of each respective ECG electrode is performed in the course of determining the respective capacitive component for each respective contact impedance of each respective ECG electrode.

8. The ECG system of claim 5, further comprising an alarm generator to sound an audio alarm or present a visual alarm.

9. The ECG system of claim 5, further comprising a display.

10. The ECG system of claim 9 wherein the display:

presents at least a portion of a user interface when the ECG system is in use; or presents a visual alarm when the alarm is issued; or both presents at least the portion of the user interface when the ECG system is in use and presents the visual alarm when the alarm is issued.

11. A non-transitory computer readable medium encoded with instructions that, when executed by a processor, perform a method comprising:

monitoring a plurality of Electrocardiogram ("ECG") electrodes ostensibly electrically connected to a human body;

driving a plurality of electrical currents through the monitored ECG electrodes in a predetermined pattern;

determining a respective contact impedance for each of the ECG electrodes as the electrical currents are driven through the ECG electrodes in the predetermined pattern, each respective contact impedance including a resistive component and a capacitive component, including determining the respective resistive component and the respective capacitive component for each respective contact impedance of each respective ECG electrode, the determining including:

selecting a first reference ECG electrode from among the plurality of ECG electrodes, the remainder of the ECG electrodes becoming non-reference ECG electrodes;

determining the respective contact impedance for each of the non-reference ECG electrodes from a first transition from a respective first ECG electrode voltage to a respective second ECG electrode voltage as the plurality of electrical currents driven through the ECG electrodes change, each respective contact impedance including a resistive component and a capacitive component;

selecting a second reference ECG electrode from among the ECG electrodes, the second reference ECG electrode being different from the first reference ECG electrode, the rest of the ECG electrodes becoming second non-reference ECG electrodes; and determining the respective contact impedance for the non-reference ECG electrode previously identified as the first reference electrode from a second transition from a respective second ECG electrode voltage to a respective third ECG electrode voltage as the electrical currents driven through the ECG electrodes changes, the respective contact impedance including a resistive component and a capacitive component;

ascertaining whether any of the determined respective contact impedances exceeds a predetermined threshold;

when any of the determined respective contact impedances exceeds the predetermined threshold exceeds the predetermined threshold, issuing a lead-off alarm.

12. The non-transitory computer readable medium of claim 11, wherein monitoring the plurality of ECG electrodes in the method includes monitoring a plurality of ECG electrodes in a 10 electrode, 12 lead configuration or in a six electrode, six lead configuration.

13. The non-transitory computer readable medium of claim 11, wherein determining the respective resistive component for each respective contact impedance of each respective ECG electrode in the method is performed in the course of determining the respective capacitive component for each respective contact impedance of each respective ECG electrode.

14. The non-transitory computer readable medium of claim 11, wherein issuing the alarm in the method includes:

sounding an audio alarm; or presenting a visual alarm; or a combination of sounding the audio alarm and presenting the visual alarm.

* * * * *